(12) United States Patent
Schultz et al.

(10) Patent No.: US 9,662,169 B2
(45) Date of Patent: May 30, 2017

(54) CATHETER WITH FLOW BALANCING VALVE

(75) Inventors: Jeffrey W. Schultz, Chino, CA (US); Michael Olen Zirkle, Yorba Linda, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 936 days.

(21) Appl. No.: 13/194,937

(22) Filed: Jul. 30, 2011

(65) Prior Publication Data

US 2013/0030385 A1    Jan. 31, 2013

(51) Int. Cl.
| | |
|---|---|
| *A61B 1/015* | (2006.01) |
| *A61B 18/14* | (2006.01) |
| *A61B 18/00* | (2006.01) |
| *A61B 18/12* | (2006.01) |

(52) U.S. Cl.
CPC ...... *A61B 18/1492* (2013.01); *A61B 2018/00029* (2013.01); *A61B 2018/0066* (2013.01); *A61B 2018/00357* (2013.01); *A61B 2018/00577* (2013.01); *A61B 2018/00744* (2013.01); *A61B 2018/00779* (2013.01); *A61B 2018/124* (2013.01); *A61B 2218/002* (2013.01)

(58) Field of Classification Search
CPC .... A61B 2018/00577; A61B 2018/025; A61B 2018/0256; A61B 18/1492; A61B 2018/0066; A61B 2018/00029; A61B 2018/0074; A61B 2018/124; A61B 2218/002; A61B 5/0422; A61B 18/1815; A61B 2217/007
USPC .................................................... 606/32–50
See application file for complete search history.

(56) References Cited

U.S. PATENT DOCUMENTS

| | | |
|---|---|---|
| 3,971,364 A | 7/1976 | Fletcher et al. |
| 4,488,561 A | 12/1984 | Doring |
| 4,764,114 A | 8/1988 | Jeffcoat et al. |
| 4,856,993 A | 8/1989 | Maness et al. |
| 4,917,102 A | 4/1990 | Miller et al. |
| 4,917,104 A | 4/1990 | Rebell |
| 5,263,493 A | 11/1993 | Avitall |

(Continued)

FOREIGN PATENT DOCUMENTS

| | | |
|---|---|---|
| CN | 101766502 A | 7/2010 |
| CN | 201595926 U | 10/2010 |

(Continued)

OTHER PUBLICATIONS

Extended European Search Report in European Application No. 13178078.5, dated Oct. 2, 2013, 4 pgs.

(Continued)

*Primary Examiner* — Ronald Hupczey, Jr.
*Assistant Examiner* — Yasamin Ekrami
(74) *Attorney, Agent, or Firm* — Lewis Roca Rothgerber Christie LLP

(57) ABSTRACT

A catheter has at least two irrigated ablation electrodes and a coaxial irrigation tubing to transport fluid to the electrodes by separate and dedicated flow paths. A valve is used to control flow of fluid into the coaxial irrigation tubing by means of a plunger assembly that allows fluid to flow through one lumen of the coaxial irrigation tubing while regulating the flow into the other lumen of the coaxial irrigation tubing in response to the fluid flow rate and pressure applied to the plunger assembly.

4 Claims, 13 Drawing Sheets

(56) References Cited

U.S. PATENT DOCUMENTS

| | | | | |
|---|---|---|---|---|
| 5,334,193 A | | 8/1994 | Nardella | |
| 5,354,291 A | * | 10/1994 | Bales ................. A61M 1/0045 604/22 | |
| 5,368,564 A | | 11/1994 | Savage | |
| 5,391,199 A | | 2/1995 | Ben-Haim | |
| 5,403,311 A | * | 4/1995 | Abele et al. ..................... 606/49 | |
| 5,487,757 A | | 1/1996 | Truckai et al. | |
| 5,499,542 A | | 3/1996 | Morlan | |
| 5,558,091 A | | 9/1996 | Acker et al. | |
| 5,563,354 A | | 10/1996 | Kropp | |
| 5,643,197 A | | 7/1997 | Brucker et al. | |
| 5,662,124 A | | 9/1997 | Wilk | |
| 5,673,695 A | | 10/1997 | McGee et al. | |
| 5,680,860 A | | 10/1997 | Imran | |
| 5,685,878 A | | 11/1997 | Falwell et al. | |
| 5,697,927 A | * | 12/1997 | Imran et al. ..................... 606/41 | |
| 5,718,701 A | | 2/1998 | Shai et al. | |
| 5,730,127 A | | 3/1998 | Avitall | |
| 5,769,843 A | | 6/1998 | Abela et al. | |
| 5,820,591 A | | 10/1998 | Thompson et al. | |
| 5,826,576 A | | 10/1998 | West | |
| 5,836,894 A | | 11/1998 | Sarvazyan | |
| 5,860,920 A | | 1/1999 | McGee et al. | |
| 5,860,974 A | | 1/1999 | Abele | |
| 5,865,815 A | | 2/1999 | Tihon | |
| 5,871,523 A | | 2/1999 | Fleischman et al. | |
| 5,876,398 A | | 3/1999 | Mulier et al. | |
| 5,902,248 A | | 5/1999 | Millar et al. | |
| 5,913,854 A | | 6/1999 | Maguire et al. | |
| 5,916,147 A | | 6/1999 | Boury | |
| 5,938,694 A | | 8/1999 | Jaraczewski et al. | |
| 5,944,022 A | | 8/1999 | Nardella et al. | |
| 5,964,757 A | | 10/1999 | Ponzi | |
| 5,974,320 A | | 10/1999 | Ward et al. | |
| 5,983,126 A | | 11/1999 | Wittkampf | |
| 6,002,955 A | | 12/1999 | Willems et al. | |
| 6,048,329 A | | 4/2000 | Thompson et al. | |
| 6,063,022 A | | 5/2000 | Ben-Haim | |
| 6,064,902 A | | 5/2000 | Haissaguerre et al. | |
| 6,123,699 A | | 9/2000 | Webster, Jr. | |
| 6,171,277 B1 | | 1/2001 | Ponzi | |
| 6,177,792 B1 | | 1/2001 | Govari et al. | |
| 6,183,463 B1 | | 2/2001 | Webster, Jr. | |
| 6,198,974 B1 | * | 3/2001 | Webster, Jr. .................. 607/122 | |
| 6,201,387 B1 | | 3/2001 | Govari | |
| 6,203,493 B1 | | 3/2001 | Ben-Haim | |
| 6,216,027 B1 | | 4/2001 | Willis et al. | |
| 6,226,542 B1 | | 5/2001 | Reisfeld | |
| 6,239,724 B1 | | 5/2001 | Doron et al. | |
| 6,241,724 B1 | | 6/2001 | Fleischman et al. | |
| 6,267,781 B1 | | 7/2001 | Tu | |
| 6,272,371 B1 | | 8/2001 | Shlomo | |
| 6,272,672 B1 | | 8/2001 | Conway | |
| 6,301,496 B1 | | 10/2001 | Reisfeld | |
| 6,332,089 B1 | | 12/2001 | Acker et al. | |
| 6,335,617 B1 | | 1/2002 | Osadchy et al. | |
| 6,371,955 B1 | | 4/2002 | Fuimaono et al. | |
| 6,436,059 B1 | | 8/2002 | Zanelli | |
| 6,456,864 B1 | | 9/2002 | Swanson et al. | |
| 6,468,260 B1 | | 10/2002 | Bumbalough et al. | |
| 6,484,118 B1 | | 11/2002 | Govari | |
| 6,500,167 B1 | | 12/2002 | Webster, Jr. | |
| 6,522,930 B1 | | 2/2003 | Schaer et al. | |
| 6,522,933 B2 | | 2/2003 | Nguyen | |
| 6,551,302 B1 | | 4/2003 | Rosinko et al. | |
| 6,574,492 B1 | | 6/2003 | Ben-Haim et al. | |
| 6,584,856 B1 | | 7/2003 | Biter et al. | |
| 6,592,581 B2 | | 7/2003 | Bowe | |
| 6,602,242 B1 | | 8/2003 | Fung et al. | |
| 6,612,992 B1 | | 9/2003 | Hossack et al. | |
| 6,618,612 B1 | | 9/2003 | Acker et al. | |
| 6,638,275 B1 | * | 10/2003 | McGaffigan et al. ........... 606/41 | |
| 6,669,692 B1 | | 12/2003 | Nelson et al. | |
| 6,690,963 B2 | | 2/2004 | Ben-Haim et al. | |
| 6,695,808 B2 | | 2/2004 | Tom | |
| 6,706,039 B2 | * | 3/2004 | Mulier et al. ................... 606/41 | |
| 6,711,429 B1 | | 3/2004 | Gilboa et al. | |
| 6,712,815 B2 | | 3/2004 | Sampson et al. | |
| 6,723,094 B1 | | 4/2004 | Desinger | |
| 6,727,371 B2 | | 4/2004 | Müller et al. | |
| 6,814,733 B2 | | 11/2004 | Schwartz et al. | |
| 6,835,173 B2 | | 12/2004 | Couvillon, Jr. | |
| 6,892,091 B1 | | 5/2005 | Ben-Haim et al. | |
| 6,908,464 B2 | | 6/2005 | Jenkins et al. | |
| 6,911,019 B2 | | 6/2005 | Mulier et al. | |
| 6,915,149 B2 | | 7/2005 | Ben-Haim | |
| 6,945,956 B2 | | 9/2005 | Waldhauser et al. | |
| 6,964,205 B2 | | 11/2005 | Papakostas et al. | |
| 6,973,339 B2 | | 12/2005 | Govari | |
| 6,984,232 B2 | | 1/2006 | Vanney et al. | |
| 6,987,995 B2 | | 1/2006 | Drysen | |
| 6,997,924 B2 | | 2/2006 | Schwartz et al. | |
| 7,008,401 B2 | | 3/2006 | Thompson et al. | |
| 7,008,418 B2 | | 3/2006 | Hall et al. | |
| 7,077,823 B2 | | 7/2006 | McDaniel | |
| 7,104,989 B2 | * | 9/2006 | Skarda ............................ 606/41 | |
| 7,156,816 B2 | | 1/2007 | Schwartz et al. | |
| 7,235,070 B2 | | 6/2007 | Vanney | |
| 7,276,061 B2 | | 10/2007 | Schaer et al. | |
| 7,285,116 B2 | * | 10/2007 | de la Rama et al. ........... 606/27 | |
| 7,285,119 B2 | | 10/2007 | Stewart et al. | |
| 7,306,593 B2 | | 12/2007 | Keidar et al. | |
| 7,311,704 B2 | | 12/2007 | Paul et al. | |
| 7,397,364 B2 | | 7/2008 | Govari | |
| 7,419,489 B2 | | 9/2008 | Vanney et al. | |
| 7,481,774 B2 | | 1/2009 | Brockway et al. | |
| 7,496,394 B2 | * | 2/2009 | Ahmed et al. ................. 600/381 | |
| 7,517,349 B2 | | 4/2009 | Truckai et al. | |
| 7,536,218 B2 | | 5/2009 | Govari et al. | |
| 7,591,816 B2 | * | 9/2009 | Wang et al. ..................... 606/41 | |
| 7,604,605 B2 | | 10/2009 | Zvuloni | |
| 7,681,432 B2 | | 3/2010 | Hay et al. | |
| 7,686,767 B2 | | 3/2010 | Maschke | |
| 7,850,685 B2 | * | 12/2010 | Kunis et al. ..................... 606/41 | |
| 8,066,702 B2 | | 11/2011 | Rittman, III et al. | |
| 8,083,691 B2 | | 12/2011 | Goldenberg et al. | |
| 8,359,082 B2 | * | 1/2013 | Selkee ............................ 600/374 | |
| 8,628,526 B2 | | 1/2014 | Laufer et al. | |
| 8,747,351 B2 | | 6/2014 | Schultz | |
| 9,220,433 B2 | | 12/2015 | Ditter et al. | |
| 9,220,868 B2 | | 12/2015 | Schultz | |
| 2001/0007070 A1 | | 7/2001 | Stewart et al. | |
| 2001/0047129 A1 | | 11/2001 | Hall et al. | |
| 2001/0047133 A1 | | 11/2001 | Gilboa et al. | |
| 2002/0002329 A1 | | 1/2002 | Avitall | |
| 2002/0022839 A1 | | 2/2002 | Stewart et al. | |
| 2002/0065455 A1 | | 5/2002 | Ben-Haim et al. | |
| 2002/0068866 A1 | | 6/2002 | Zikorus et al. | |
| 2002/0165461 A1 | | 11/2002 | Hayzelden et al. | |
| 2002/0169444 A1 | | 11/2002 | Mest et al. | |
| 2002/0193781 A1 | | 12/2002 | Loeb | |
| 2003/0060822 A1 | | 3/2003 | Schaer et al. | |
| 2003/0105453 A1 | | 6/2003 | Stewart et al. | |
| 2003/0120195 A1 | | 6/2003 | Milo et al. | |
| 2003/0130615 A1 | | 7/2003 | Tom | |
| 2003/0158494 A1 | | 8/2003 | Dahl et al. | |
| 2003/0216722 A1 | | 11/2003 | Swanson | |
| 2004/0049255 A1 | | 3/2004 | Jain et al. | |
| 2004/0064024 A1 | | 4/2004 | Sommer | |
| 2004/0068178 A1 | | 4/2004 | Govari | |
| 2004/0082948 A1 | | 4/2004 | Stewart et al. | |
| 2004/0097806 A1 | | 5/2004 | Hunter et al. | |
| 2004/0102769 A1 | | 5/2004 | Schwartz et al. | |
| 2004/0143175 A1 | | 7/2004 | Coleman et al. | |
| 2004/0147920 A1 | | 7/2004 | Keidar | |
| 2004/0152974 A1 | | 8/2004 | Solomon | |
| 2004/0158141 A1 | | 8/2004 | Scheib | |
| 2004/0244464 A1 | | 12/2004 | Hajdukiewicz et al. | |
| 2004/0254458 A1 | | 12/2004 | Govari | |
| 2005/0004565 A1 | | 1/2005 | Vanney | |
| 2005/0010095 A1 | | 1/2005 | Stewart et al. | |
| 2005/0033135 A1 | | 2/2005 | Govari | |
| 2005/0070894 A1 | | 3/2005 | McClurken | |
| 2005/0080429 A1 | | 4/2005 | Freyman et al. | |

(56) References Cited

U.S. PATENT DOCUMENTS

| | | |
|---|---|---|
| 2005/0165388 A1* | 7/2005 | Bhola ........................... 606/14 |
| 2005/0187544 A1 | 8/2005 | Swanson et al. |
| 2005/0277875 A1 | 12/2005 | Selkee |
| 2006/0009690 A1 | 1/2006 | Fuimaono et al. |
| 2006/0009735 A1 | 1/2006 | Viswanathan et al. |
| 2006/0015096 A1 | 1/2006 | Hauck et al. |
| 2006/0020264 A1 | 1/2006 | Crowley et al. |
| 2006/0106295 A1 | 5/2006 | Jais et al. |
| 2006/0173480 A1 | 8/2006 | Zhang |
| 2006/0200049 A1 | 9/2006 | Leo et al. |
| 2006/0235381 A1 | 10/2006 | Whayne et al. |
| 2006/0241366 A1 | 10/2006 | Falwell et al. |
| 2006/0247618 A1 | 11/2006 | Kaplan et al. |
| 2006/0253116 A1 | 11/2006 | Avitall et al. |
| 2007/0021742 A1 | 1/2007 | Viswanathan |
| 2007/0060832 A1 | 3/2007 | Levin |
| 2007/0060847 A1 | 3/2007 | Leo et al. |
| 2007/0100332 A1 | 5/2007 | Paul et al. |
| 2007/0106114 A1 | 5/2007 | Sugimoto et al. |
| 2007/0142749 A1 | 6/2007 | Khatib et al. |
| 2007/0151391 A1 | 7/2007 | Larkin et al. |
| 2007/0156114 A1 | 7/2007 | Worley et al. |
| 2007/0161882 A1 | 7/2007 | Pappone |
| 2007/0179492 A1 | 8/2007 | Pappone |
| 2007/0185397 A1 | 8/2007 | Govari et al. |
| 2007/0191829 A1 | 8/2007 | McGee et al. |
| 2007/0197939 A1 | 8/2007 | Wallace et al. |
| 2007/0282211 A1 | 12/2007 | Ofek et al. |
| 2008/0009750 A1 | 1/2008 | Aeby et al. |
| 2008/0015568 A1 | 1/2008 | Paul et al. |
| 2008/0051704 A1 | 2/2008 | Patel et al. |
| 2008/0065111 A1 | 3/2008 | Blumenkranz et al. |
| 2008/0071267 A1 | 3/2008 | Wang et al. |
| 2008/0077049 A1 | 3/2008 | Hirshman |
| 2008/0097394 A1 | 4/2008 | Lampropoulos et al. |
| 2008/0161774 A1 | 7/2008 | Hastings et al. |
| 2008/0161795 A1 | 7/2008 | Wang et al. |
| 2008/0161803 A1 | 7/2008 | Oral et al. |
| 2008/0183075 A1 | 7/2008 | Govari et al. |
| 2008/0249522 A1 | 10/2008 | Pappone et al. |
| 2008/0255540 A1 | 10/2008 | Selkee |
| 2008/0275428 A1 | 11/2008 | Tegg et al. |
| 2008/0275442 A1 | 11/2008 | Paul et al. |
| 2008/0275465 A1 | 11/2008 | Paul et al. |
| 2008/0281319 A1 | 11/2008 | Paul et al. |
| 2008/0287777 A1 | 11/2008 | Li et al. |
| 2008/0288038 A1 | 11/2008 | Paul et al. |
| 2008/0294144 A1 | 11/2008 | Leo et al. |
| 2008/0294158 A1 | 11/2008 | Pappone et al. |
| 2009/0010021 A1 | 1/2009 | Smith et al. |
| 2009/0062787 A1* | 3/2009 | Schaer et al. ................... 606/41 |
| 2009/0093806 A1 | 4/2009 | Govari et al. |
| 2009/0118729 A1* | 5/2009 | Auth ................. A61B 18/1492 606/42 |
| 2009/0138007 A1 | 5/2009 | Govari et al. |
| 2009/0158511 A1 | 6/2009 | Maze et al. |
| 2009/0254083 A1 | 10/2009 | Wallace et al. |
| 2009/0287118 A1 | 11/2009 | Malek |
| 2009/0306650 A1 | 12/2009 | Govari et al. |
| 2010/0030209 A1 | 2/2010 | Govari et al. |
| 2010/0063478 A1 | 3/2010 | Selkee |
| 2010/0137845 A1 | 6/2010 | Ramstein et al. |
| 2010/0145423 A1 | 6/2010 | Seifert |
| 2010/0152574 A1 | 6/2010 | Erdman et al. |
| 2010/0168548 A1 | 7/2010 | Govari et al. |
| 2010/0168620 A1 | 7/2010 | Klimovitch et al. |
| 2010/0168918 A1 | 7/2010 | Zhao et al. |
| 2010/0222851 A1 | 9/2010 | Deem et al. |
| 2010/0222859 A1 | 9/2010 | Govari et al. |
| 2011/0034989 A1 | 2/2011 | Al-Marashi et al. |
| 2011/0054287 A1 | 3/2011 | Schultz |
| 2011/0054446 A1 | 3/2011 | Schultz |
| 2011/0118582 A1 | 5/2011 | De la Rama et al. |
| 2011/0130648 A1 | 6/2011 | Beeckler et al. |
| 2011/0144639 A1 | 6/2011 | Govari |
| 2011/0160719 A1 | 6/2011 | Govari et al. |
| 2011/0184406 A1 | 7/2011 | Selkee |
| 2011/0306851 A1 | 12/2011 | Wang |
| 2012/0053403 A1 | 3/2012 | Ducharme et al. |
| 2012/0116200 A1 | 5/2012 | Roy et al. |
| 2012/0116382 A1 | 5/2012 | Ku et al. |
| 2012/0143088 A1 | 6/2012 | Schultz |
| 2012/0172703 A1 | 7/2012 | Esguerra et al. |
| 2012/0245577 A1 | 9/2012 | Mihalik et al. |
| 2012/0323174 A1 | 12/2012 | Shih |
| 2013/0006238 A1 | 1/2013 | Ditter et al. |
| 2013/0165922 A1 | 6/2013 | Falwell et al. |
| 2013/0304047 A1 | 11/2013 | Grunewald et al. |
| 2013/0304061 A1 | 11/2013 | Chang et al. |
| 2013/0304062 A1 | 11/2013 | Chan et al. |
| 2015/0265345 A1 | 9/2015 | Bui et al. |

FOREIGN PATENT DOCUMENTS

| | | |
|---|---|---|
| CN | 201595926 U | 10/2010 |
| CN | 102000379 A | 4/2011 |
| CN | 202020532 U | 11/2011 |
| CN | 102846374 A | 1/2013 |
| DE | 197 50 441 A1 | 6/1999 |
| EP | 0 856 292 A1 | 8/1998 |
| EP | 0 928 601 A1 | 7/1999 |
| EP | 1 042 990 A1 | 10/2000 |
| EP | 1 181 896 A1 | 2/2002 |
| EP | 1 502 555 A1 | 2/2005 |
| EP | 1 586 281 A1 | 10/2005 |
| EP | 1 690 564 A1 | 8/2006 |
| EP | 1 743 575 A2 | 1/2007 |
| EP | 1 820 464 A1 | 8/2007 |
| EP | 1 897 581 A2 | 3/2008 |
| EP | 2 000 789 A2 | 12/2008 |
| EP | 2 047 797 A2 | 4/2009 |
| EP | 2 127 604 A1 | 12/2009 |
| EP | 2 130 508 A2 | 12/2009 |
| EP | 2 171 240 | 4/2010 |
| EP | 2 229 904 A1 | 9/2010 |
| EP | 2 263 588 A2 | 12/2010 |
| EP | 2 289 403 A1 | 3/2011 |
| EP | 2 289 408 A1 | 3/2011 |
| EP | 2289408 A1 | 3/2011 |
| EP | 2 338 411 A1 | 6/2011 |
| EP | 2 338 412 A1 | 6/2011 |
| EP | 2 380 518 A2 | 10/2011 |
| EP | 2263588 A3 | 7/2012 |
| EP | 2 540 245 A1 | 2/2013 |
| JP | 2005-345215 A | 12/2005 |
| JP | 2006-064465 A | 3/2006 |
| WO | WO 95/10326 A1 | 4/1995 |
| WO | WO 96/05768 | 2/1996 |
| WO | WO 97/29678 A2 | 8/1997 |
| WO | WO 97/29709 A1 | 8/1997 |
| WO | WO 97/29710 A1 | 8/1997 |
| WO | WO 98/29032 A1 | 7/1998 |
| WO | WO 99/56812 | 11/1999 |
| WO | WO 03/020139 A2 | 3/2003 |
| WO | WO 2006/003216 A1 | 1/2006 |
| WO | WO 2006/029563 A1 | 3/2006 |
| WO | WO 2006/086152 A2 | 8/2006 |
| WO | WO 2006/092563 A1 | 9/2006 |
| WO | WO 2007/025230 A2 | 3/2007 |
| WO | WO 2007/050960 A2 | 5/2007 |
| WO | WO 2007/067938 A2 | 6/2007 |
| WO | WO 2007/082216 A1 | 7/2007 |
| WO | WO 2007/098494 A1 | 8/2007 |
| WO | WO 2007/111182 A1 | 10/2007 |
| WO | WO 2009/078280 A1 | 6/2009 |
| WO | WO 2009/085470 A1 | 7/2009 |
| WO | WO 2009/147399 A1 | 12/2009 |
| WO | WO 2010/008975 A2 | 1/2010 |

OTHER PUBLICATIONS

European Patent Office Extended Search Report for EP 12178339.3, dated Dec. 13, 2012, 8 pgs.

(56) References Cited

OTHER PUBLICATIONS

Biter, W.J. et al., "Magnetic Wire Strain Sensor," 33rd International SAMPE Technical Conference, Nov. 5-8, 2001, vol. 33, Cover pg. and pp. 12-23, Seattle, WA.
Biter, W.J. et al., "Magnetic Wire for Monitoring Strain in Composites," *Sensors*, Jun. 2001, www.sensormag.com, pp. 110-114.
Okumura, Y. et al., "A Systematic Analysis of In Vivo Contact Forces on Virtual Catheter Tip/Tissue Surface Contact During Cardiac Mapping and Intervention," *Journal of Cardiovascular Electrophysiology*, vol. 19, No. 6, pp. 632-640, Jun. 2008.
European Patent Office Search Report for EP 12178339.3, dated Oct. 31, 2012, 5 pgs.
European Search Report, for corresponding Patent Application No. EP 13 16 7733, dated Aug. 14, 2013, 3 pages.
European Search Report for Application No. EP 12174272.0, dated Sep. 25, 2012, 6 pages.
Chinese Office action dated Mar. 5, 2014 in Chinese Application No. 201010624677.4, English language translation only, 14 pages.
Russian Office action dated Nov. 14, 2013 in Russian Application No. 2009149447/14(073080) with English translation, 12 pages.
Russian Office action dated Dec. 5, 2013 in Russian Application No. 2012127341/15(042535), English language translation only, 3 pages.
English Translation of SIPO, P.R. China Office Action dated Jul. 31, 2015 for Chinese Patent Application No. 201210269015.9, 3 pages.
European Search Report dated Aug. 14, 2013 for European Patent Application No. 13167733, 3 pages.
European Examination Report dated Nov. 25, 2014 for European Patent Application No. 13167733.8, 8 pages.
SIPO Office action dated Apr. 27, 2016 in corresponding CN application No. 201310176320.8, with English translation, 20 pages.
European Examination Report dated Apr. 21, 2016 in corresponding Application No. EP 14174792.3, 6 pages.
Extended European Search Report dated Jan. 4, 2016, issued in EP Application No. 15179939.2, 8 pages.

\* cited by examiner

| CONDITION | TIP ELECTRODE FLOW RATE (mL/min) | RING ELECTRODE FLOW RATE (mL/min) | TOTAL FLOW RATE (mL/min)* |
|---|---|---|---|
| Maintenance Flow | 2 | 2 | 8 |
| Focal Ablation from Tip Electrode | 15 | 2 | 21 |
| Linear Ablation from All Tip and Ring Electrodes | 15 | 6 | 33 |

* value based on 3 ring electrodes

FIG. 13

CATHETER WITH FLOW BALANCING VALVE

FIELD OF INVENTION

This invention relates generally to methods and devices for invasive medical treatment, and specifically to catheters, in particular, irrigated ablation catheters.

BACKGROUND

Ablation of myocardial tissue is well known as a treatment for cardiac arrhythmias. In radio-frequency (RF) ablation, for example a catheter is inserted into the heart and brought into contact with tissue at a target location. RF energy is then applied through electrodes on the catheter in order to create a lesion for the purpose of breaking arrhythmogenic current paths in the tissue.

Ablation has been accomplished primarily by means of focal ablation, that is, ablation by a tip electrode at a distal end of the catheter. Thus, for linear ablation along a line or curve, the tip electrode is repositioned repeatedly or dragged across the tissue along the line or curve during a prolonged ablation.

Also known are irrigated ablation tip and ring electrodes which are effective at reducing electrode temperature during ablation to minimize the formation of char and coagulum. However, fluid load on the patient is a concern, especially where multiple electrodes are being irrigated.

Current EP catheters utilize a single irrigation lumen to deliver irrigation to one or more irrigated electrodes. Pump units consisting of one pump head are therefore used. As catheters become more complex, the need for multiple irrigation lumens becomes more critical. Currently, irrigation delivery to a catheter with multiple irrigation lumens requires the use of multiple pump units.

Accordingly, there is a desire for a catheter adapted for both focal and linear ablation for accomplishing linear lesions without repositioning of the catheter. In particular, there is a desire for a catheter with tip and ring electrodes that can provide irrigation fluid to different electrodes at different flow rates without the need for multiple pumps.

SUMMARY OF THE INVENTION

The present invention is directed to an irrigated catheter with at least two lumens through which irrigation is delivered, and a valve that balances flow to the two lumens. In the case of a linear ablation catheter (that is, a catheter adapted to form a generally continuous elongated lesion) where a tip electrode irrigated by one fluid lumen and a plurality of ring electrodes irrigated by another fluid lumen, fluid is pumped to the catheter whereby flow to the tip electrode and the set of ring electrodes is controlled without use of external inputs or adjustments. The desired flow control is accomplished by the use of a coaxial irrigation tubing and a valve having a plunger assembly that adjusts the ratio of flow rates between the two irrigation lumens as total flow rate supplied to the catheter is varied.

In one embodiment, the valve has a body that houses the components of the valve. The valve includes an inlet opening and an outlet opening, where the inlet opening may be a female luer lock connector for connection to a tubing connected to a fluid source and the outlet opening may be a female end through which the coaxial irrigation tubing can extend from the control handle into the valve.

In one embodiment, the plunger assembly includes a plunger head, a spring member and a base, where the plunger head and the base have a through-hole for receiving a first lumen of the coaxial irrigation tubing to provide a first flow path through the valve along a longitudinal axis. The plunger is displaceable along the longitudinal axis to provide a second flow path that passes around the plunger. And, depending on the degree of displacement, the plunger can vary the flow rate or amount of fluid flowing through the second flow path. For example, the plunger can allow merely a leak to provide a minimum flow through the second flow path, or the plunger can allow greater flow through the second flow path. The plunger may take the form of a cone, a sphere, flat seal or any other suitable configuration for regulating flow rate. By selecting a spring member with a known constant k, the displacement of plunger as a function of fluid pressure on the plunger can be calculated and anticipated. However, while Hooke's law states that the restoring force F of a spring is directly proportional to a small displacement x (i.e. F=kx, where k is the proportionality constant for the specific spring member used), the displacement of the plunger may not necessarily be a linear function of the pressure due to the configuration of the plunger.

In a detailed embodiment, a catheter of the present invention includes an elongated body, a distal section having at least a first electrode and a second electrode, each electrode adapted for irrigation, and a control handle proximal the elongated body. Advantageously, the catheter also includes a coaxial irrigation tubing having at least an inner lumen and an outer lumen, the inner lumen is dedicated to transporting fluid to the first electrode, and the outer lumen is dedicated to transporting fluid to the second electrode.

In a detailed embodiment, a valve of the present invention includes a body defining an inlet opening, an outlet opening and an interior cavity connecting the inlet opening and the outlet opening, where the inlet opening is adapted to receive fluid flow at variable predetermined flow rates. The valve includes a plunger assembly having a plunger head, a base, and a spring member supporting the plunger head from the base at a predetermined position relative to the inlet opening. A first lumen formed extending through the plunger head and the base receives an unimpeded portion of the fluid flow entering the inlet opening to define a first flow path through the valve. The plunger head itself however diverts the remaining portion of the fluid flow toward a second flow path, the cross-section of which varies depending on the degree of displacement of the plunger head under the pressure of the fluid flow impacting on the plunger head. Thus, the body defines first and second fluid flow paths where the first fluid path includes the first lumen to the exclusion of the interior cavity, and the second fluid flow path includes the interior cavity to the exclusion of the first lumen, such that the first fluid path receives a first or main portion of a flow entering the valve via the inlet opening and the second fluid path receives a second or remainder portion of the flow entering the valve via the inlet opening. To that end, the spring member is adapted to allow the displacement of the plunger head when the inlet opening flow rate exceeds a threshold for varying at least one of the portions of flow to the first and second fluid paths.

The present invention is also directed to a system for ablation which in one embodiment includes a catheter adapted for ablation, having at least a first electrode and a second electrode, and a coaxial irrigation tubing configured with at least two separate fluid paths within the catheter to deliver fluid to each electrode. The system also includes an ablation energy generator configured to selective energize the first and second electrodes, an irrigation pump responsive to signals from the ablation energy generator indicative of an energization state of at least one electrode. Advantageously, the system further includes a valve configured to receive fluid from the fluid source for delivery to the coaxial irrigation tubing, wherein the irrigation pump is adapted to pump fluid to the catheter at a selected flow rate in accordance with the signals from ablation energy generator, and wherein the valve has a plunger assembly adapted to output two separate fluid flows at two different flow rates.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIG. 13 is a table showing sample fluid flow rates for various operating conditions of the system.

DETAILED DESCRIPTION OF THE INVENTION

Figure 1:
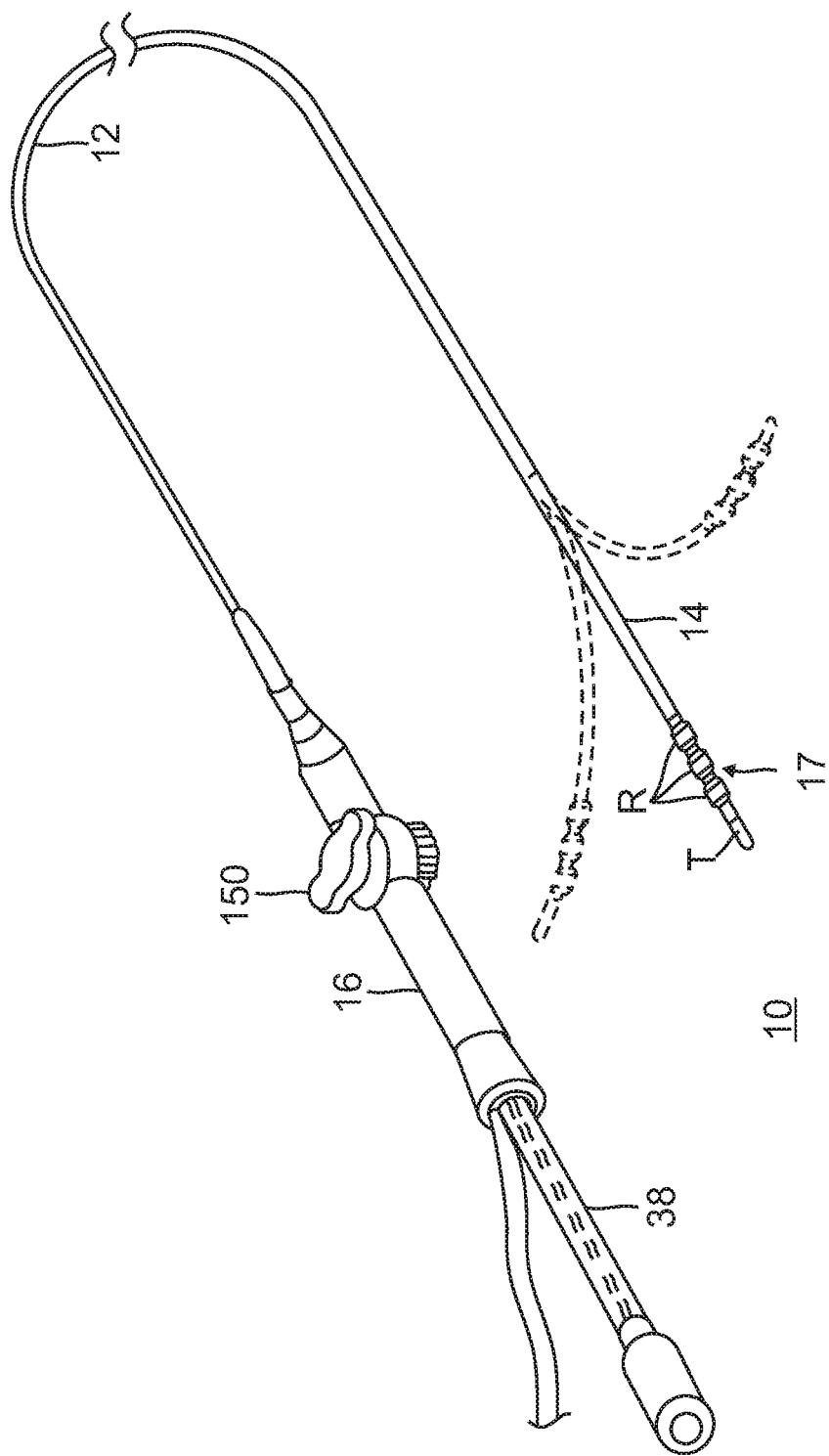
FIG. 1 is a perspective view of an embodiment of a catheter in accordance with the present invention.

As illustrated in FIG. 1, the present invention includes a steerable catheter 10 with multiple electrodes, including a tip electrode T and a plurality of ring electrodes R, with a coaxial irrigation tubing to separately deliver fluid to the tip and ring electrodes. The catheter is deployed in a target region of the body, e.g., the atria of the heart, and designed to facilitate linear ablation along target tissue by means of radiofrequency (RF) current. The catheter is advantageously designed to form a generally continuous RF lesion without the need to reposition the catheter. Once placed, the catheter can remain in position whereupon RF energy is selectively delivered through the electrodes to form the generally continuous RF lesion. In one embodiment, RF energy is delivered through each of the ring electrodes as uni-polar electrodes to the contacting target tissue to a return electrode (e.g., an external electrode patch affixed to the patient's back) to accomplish focal uni-polar lesions. Then, to "connect" the uni-polar lesions so as to form a generally continuous linear lesion, tissue in between each of the focal lesion is ablated by energizing the ring electrodes as bi-polar electrodes to form bi-polar lesions between the ring electrodes. Accordingly, the catheter allows for faster lesion formation with reduced catheter manipulation.

Figure 2:
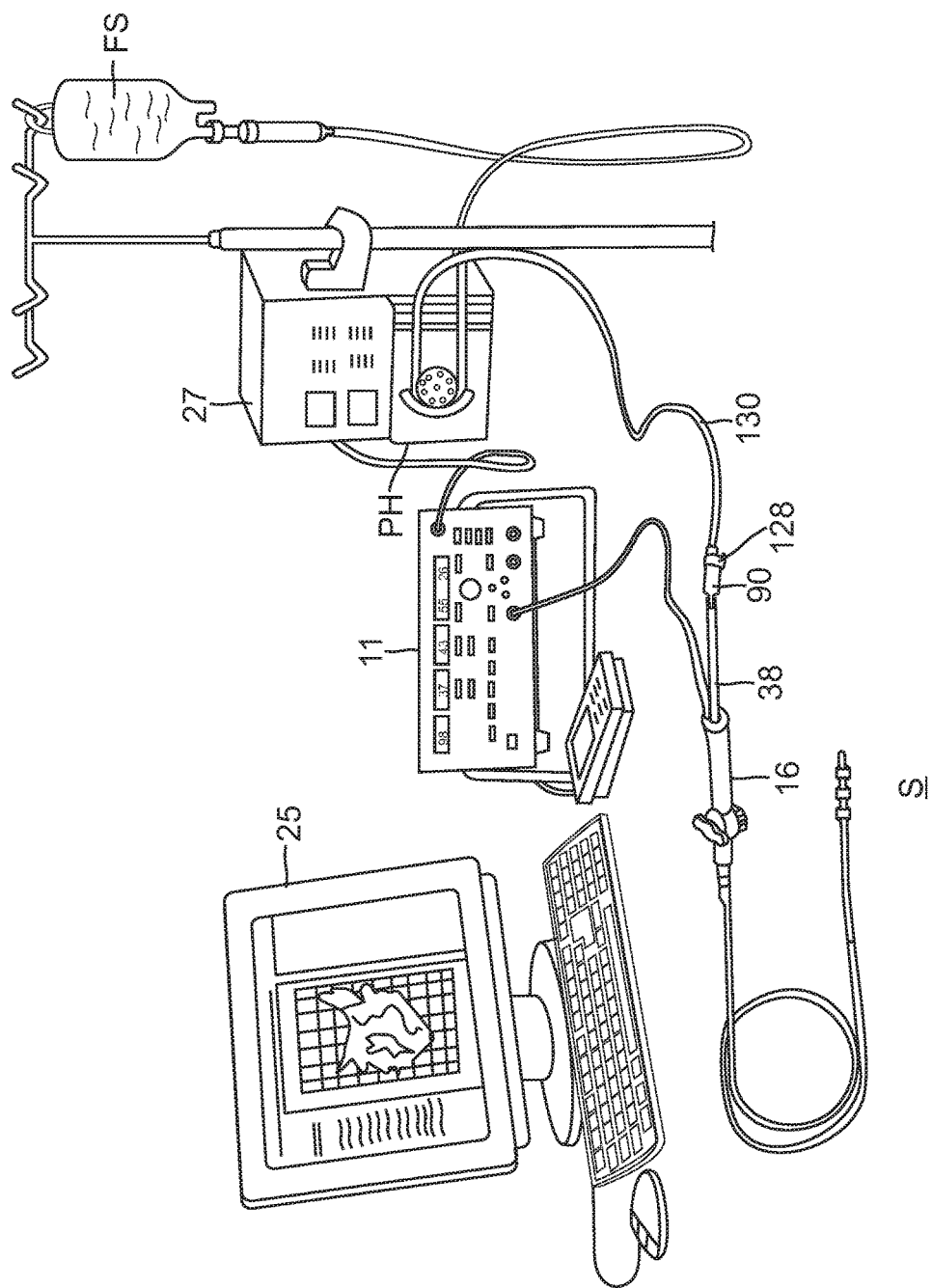
FIG. 2 is a perspective view of an embodiment of an integrated ablation system in accordance with the present invention.
Figure 3:
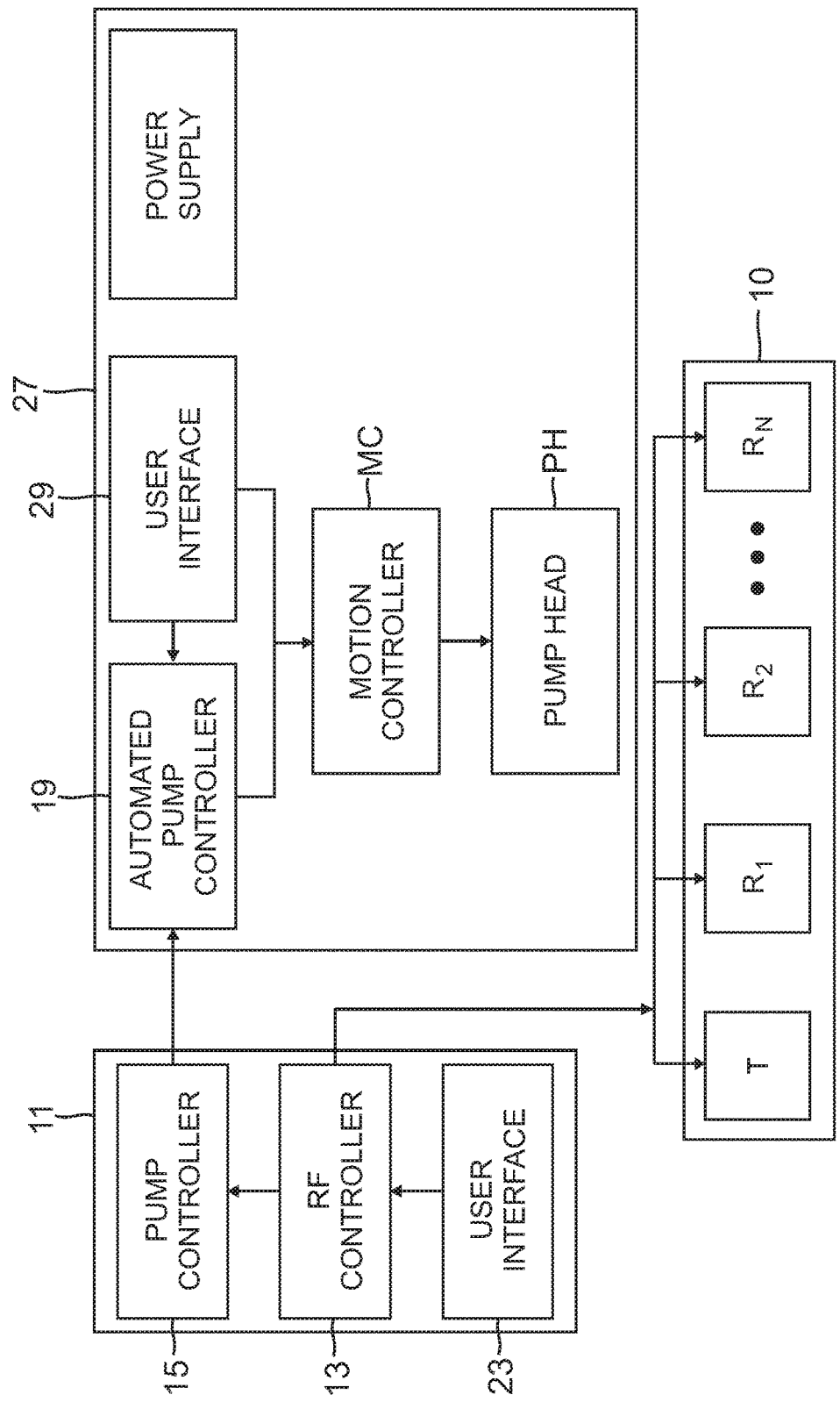
FIG. 3 is a block diagram of the system of FIG. 2.

As illustrated in FIGS. 2 and 3, the catheter 10 may be used with an integrated ablation system S which in one embodiment includes an external control system, for example, a multi-channel RF generator 11 with an RF ablation controller 13, a pump head controller 15, and a visual display 25. The system S also includes an irrigation pump 27 with an automated control receiver 19 in communication with a motion controller MC that controls a pump head PH that acts on a fluid tubing extending between a fluid source FC and a luer hub proximal of the control handle of the catheter.

The RF generator 11 has built in logic which allows for automated operation of the pump head based on ablation settings. User interface 23 on the RF generator allows the user to modify or define custom parameters for the operation of the pump for increased control over the process.

Ablation is delivered at a set wattage on the multi-channel RF generator 11. The irrigation pump 27 can be a peristaltic pump, or roller pump, using positive displacement for pumping fluids. As understood by one of ordinary skill in the art, a peristaltic pump has a flexible tube fitted inside a pump casing, which is typically circular, although a linear peristaltic pump may be used as well. Moreover, the irrigation pump may further include a bubble sensor, an occlusion sensor or any other sensor utilized for the safe operation of the pump.

The multi-channel RF generator 11 routes the RF current through selected electrodes in accordance with ablation parameters set and controlled by an operator via the user interface 23. For example, (i) all electrodes may be energized simultaneously, (ii) the tip electrode may be energized to the exclusion of all ring electrodes, and (iii) vice versa, (iv) the tip electrode may be energized in combination with selective ring electrodes, or (v) all or only selective ring electrodes may be energized. Moreover, any combination or sequence of any of these energization patterns in series is possible, all obviating the need to reposition the catheter during ablation of a linear lesion.

During ablation, the multi-channel RF generator also monitors the temperature of the electrode(s) involved and reduces the wattage if the temperature exceeds a value set by the user. Catheter temperature information is sent from a thermocouple on the catheter to the RF generator.

In accordance with the invention, the RF generator 11 also communicates with the irrigation pump 27 via the pump head controller 15 to control irrigation flow delivery in accordance with the selective energization of the electrodes for optimizing fluid flow to the catheter. Communication may be accomplished by the use of cabling, wireless communication technology, such as BLUETOOTH®, or by radio signals (e.g., transmitted at 2.4 GHz or other suitable frequency for use in a medical lab environment).

In response to ablation/energization signals generated by the RF ablation controller 13 indicating a state of energization or "Condition" of each electrode, the pump head controller 15 in communication with the RF ablation controller 13 sends appropriate signals to the automated controller receiver 19 of the irrigation pump 27 to control the motion controller MC for the pump head PH. In response to the signals, the motion controller MC may actuate the pump head PH to start or stop flow, and/or to increase or decrease the flow rate. That is, while RF energy is being delivered through one electrode or set of electrodes, the RF generator triggers the corresponding pump head to deliver fluid at a desired flow rate in accordance with the electrode(s) being energized. For example, if RF energy is being applied to all electrodes or if RF energy is increased for any electrode, the RF generator triggers the pump head to deliver fluid at a higher flow rate so as to diffuse blood in the surrounding area and minimize formation of char and coagulum due to increased electrode heating. If RF energy is being applied to fewer electrodes, the RF generator triggers the pump head to deliver fluid at a lower flow rate sufficient to irrigate the ablating electrodes while minimizing fluid load on the patient. As understood by one of ordinary skill in the art, a minimum flow rate through an inactive energized electrode is generally maintained in order to flush the irrigation apertures in the electrodes and minimize the risk of obstruction. The operator may also manually control the pump heads via the user interface 29, as desired.

Referring to FIG. 1, the catheter 10 according to the disclosed embodiments comprises an elongated body that may include an insertion shaft or catheter body 12 having a longitudinal axis, and an intermediate section 14 distal of the catheter body that can be uni- or bi-directionally deflectable off-axis from the catheter body. Distal of the intermediate section 14 is a distal section 17 carrying a distal tip electrode T and a plurality of ring electrodes R adapted for ablation and irrigation.

Figure 4A:
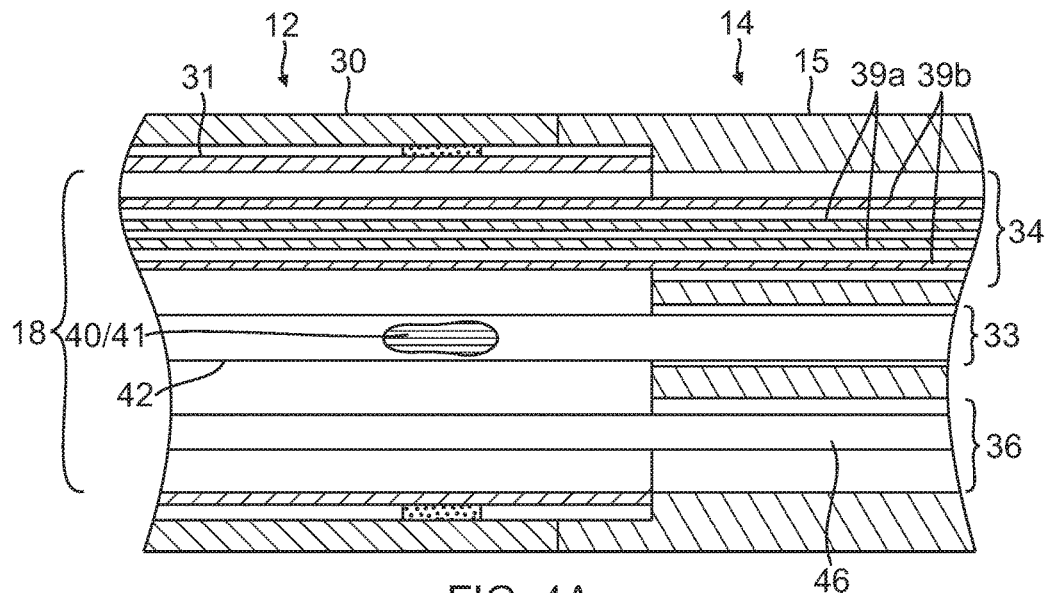
FIG. 4A is a side cross-sectional view of the catheter of FIG. 1, including a junction of a catheter body and an intermediate deflectable section, taken along one diameter.
Figure 4B:
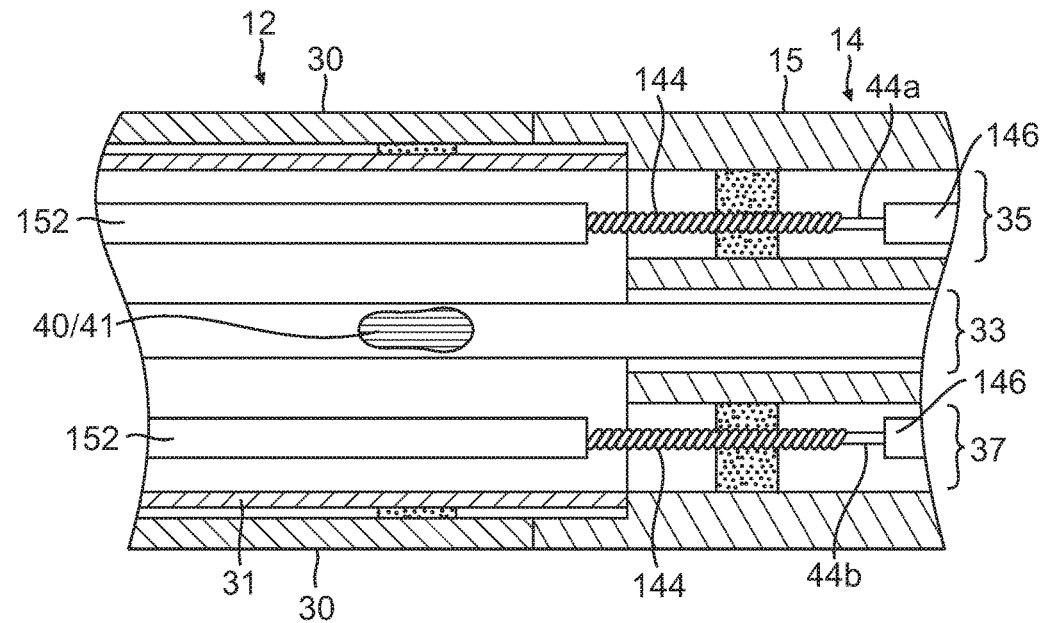
FIG. 4B is a side cross-sectional view of the catheter of FIG. 1, including a junction of a catheter body and an intermediate deflectable section, taken along another diameter.
Figure 4C:
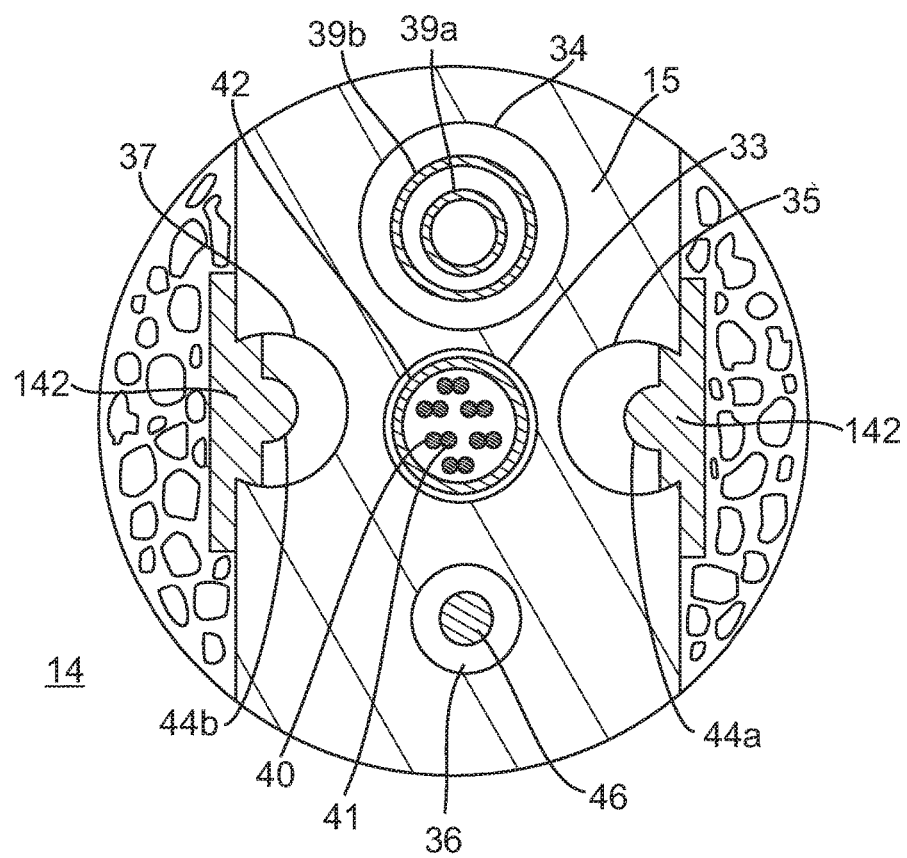
FIG. 4C is an end cross-sectional view of an embodiment of an intermediate section of the catheter of FIG. 1.

In the depicted embodiment of FIGS. 4A, 4B and 4C, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 30 made of polyurethane or PEBAX. The outer wall 30 comprises an imbedded braided mesh of stainless steel or the like, as is generally known in the art, to increase torsional stiffness of the catheter body 12 so that, when the control handle 16 is rotated, the intermediate section 14 and distal section 17 will rotate in a corresponding manner.

The outer diameter of the catheter body 12 is not critical, but is preferably no more than about 8 french, more preferably 7 french. Likewise the thickness of the outer wall 30 is not critical, but is thin enough so that the central lumen 18 can accommodate any desired wires, cables and/or tubes. The inner surface of the outer wall 30 is lined with a stiffening tube 31 to provide improved torsional stability. The outer diameter of the stiffening tube 31 is about the same as or slightly smaller than the inner diameter of the outer wall 30. The stiffening tube 31 can be made of any suitable material, such as polyimide, which provides very good stiffness and does not soften at body temperature.

The deflectable intermediate section 14 comprises a short section of tubing 15 having multiple lumens, each occupied by the various components extending through the intermediate section. In the illustrated embodiment, there are five lumens 33, 34, 35, 36 and 37 as best seen in FIG. 4C. Lead wire/thermocouple pairs 40,41 for each electrode pass through a first lumen 33 which is on-axis in the illustrated embodiment. A nonconductive protective sheath 42 is provided. A coaxial irrigation tubing 38 passes through a second lumen 34 which is off-axis in the illustrated embodiment. For at least uni-directional deflection, a first puller wire 44a passes through a third, off-axis lumen 35. A cable 46 for a position sensor assembly, including a plurality of single axis sensors (SAS) positioned on the distal section 17, passes through a fourth lumen 36 which is off-axis in the illustrated embodiment. For bi-directional deflection, a second puller wire 44 passes through a fifth, off-axis lumen 37.

The coaxial irrigation tubing 38 defines multiple coaxial lumens. In the disclosed embodiment, there are at least an inner lumen 39a and an outer lumen 39b for delivering fluid to an electrode (or a first set of electrodes) and another electrode (or a second set of electrodes), to the mutual exclusion of the each other. That is, the tubing 38 provides at least two parallel, dedicated, separated and isolated flow paths within the catheter. Fluid can be delivered simultaneously by both flow paths, or fluid can be delivered in one flow path and not the other, and vice versa.

The multi-lumened tubing 15 of the intermediate section 14 is made of a suitable non-toxic material that is preferably more flexible than the catheter body 12. A suitable material is braided polyurethane or PEBAX, i.e., polyurethane or PEBAX with an embedded mesh of braided stainless steel or the like. The plurality and size of each lumen are not critical, provided there is sufficient room to house the components extending therethrough. Position of each lumen is also not critical, except the positions of the lumens 35, 37 for the puller wires 44a, 44b. The lumens 35, 37 should be off-axis, and diametrically opposite of each other for bi-directional deflection along a plane.

The useful length of the catheter, i.e., that portion that can be inserted into the body can vary as desired. Preferably the useful length ranges from about 110 cm to about 120 cm. The length of the intermediate section 14 is a relatively small portion of the useful length, and preferably ranges from about 3.5 cm to about 10 cm, more preferably from about 5 cm to about 6.5 cm.

A preferred means for attaching the catheter body 12 to the intermediate section 14 is illustrated in FIGS. 4A and 4B. The proximal end of the intermediate section 14 comprises an inner circumferential notch that receives the outer surface of the distal end of the stiffening tube 31 of the catheter body 12. The intermediate section 14 and catheter body 12 are attached by glue or the like, for example, polyurethane. If desired, a spacer (not shown) can be provided within the catheter body 12 between the distal end of the stiffening tube 31 and the proximal end of the intermediate section 14 to provide a transition in flexibility at the junction of the catheter body 12 and the intermediate section, which allows the junction to bend smoothly without folding or kinking. An example of such a spacer is described in more detail in U.S. Pat. No. 5,964,757, the disclosure of which is incorporated herein by reference.

Figure 5:
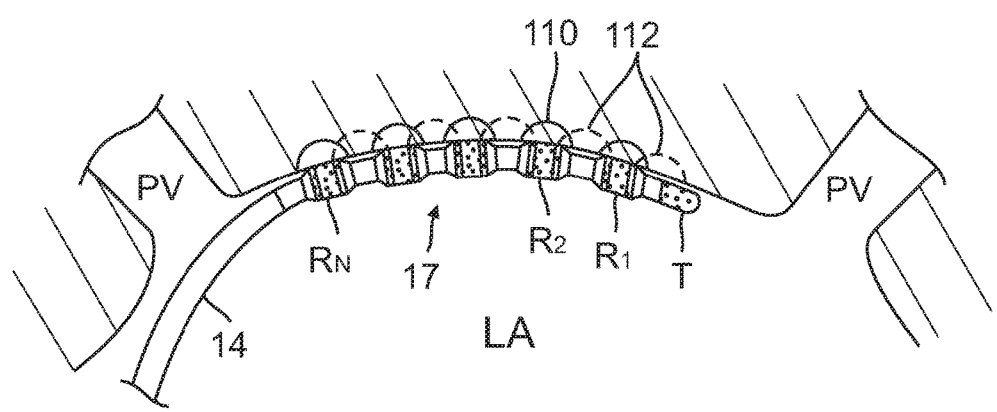
FIG. 5 is a side elevational view of an embodiment of a distal section of the catheter of FIG. 1, in contact with tissue to form lesions through ablation.

With reference to FIG. 5, distal the intermediate section 14 is the distal section 17 which includes a multi-lumened tubing 50 on which are mounted distal tip electrode T and plurality of ring electrodes R1-RN, for example, ranging between about three to nine ring electrodes. In the disclosed embodiment, there are five ring electrodes. The tubing 50 can be made of any biocompatible plastic such as polyurethane or PEBAX. In the illustrated embodiment of FIGS. 6A, 6B and 6C, the tubing 50 has three lumens 51, 52, and 53. The lead wire/thermocouple pair 40, 41 for the tip electrode passes through a first, on-axis lumen 51 which is generally in axial alignment with the first lumen 33 of the intermediate section 14. A second, off-axis lumen 52 generally in axial alignment with the second lumen 34 of the intermediate section receives a distal end of the coaxial irrigation tubing 43. The lumen 52 is sized to form a fluid-tight seal with the distal end of the tubing 43 so that fluid flows distally directly into the lumen 52. As shown in FIG. 6C, a radial opening 55 is formed in the side wall of the tubing 50 underneath each ring electrode R so that fluid flows from the outer lumen 39b of the coaxial irrigation tubing 43, into the lumen 52 of the tubing 50 and into the ring electrodes R1-RN as shown by arrows 57. The inner lumen 39a is unbreached so that fluid continues to flow toward a distal end of the catheter. A suitable irrigation ring electrode is illustrated in detail in FIG. 7.

Figure 6A:
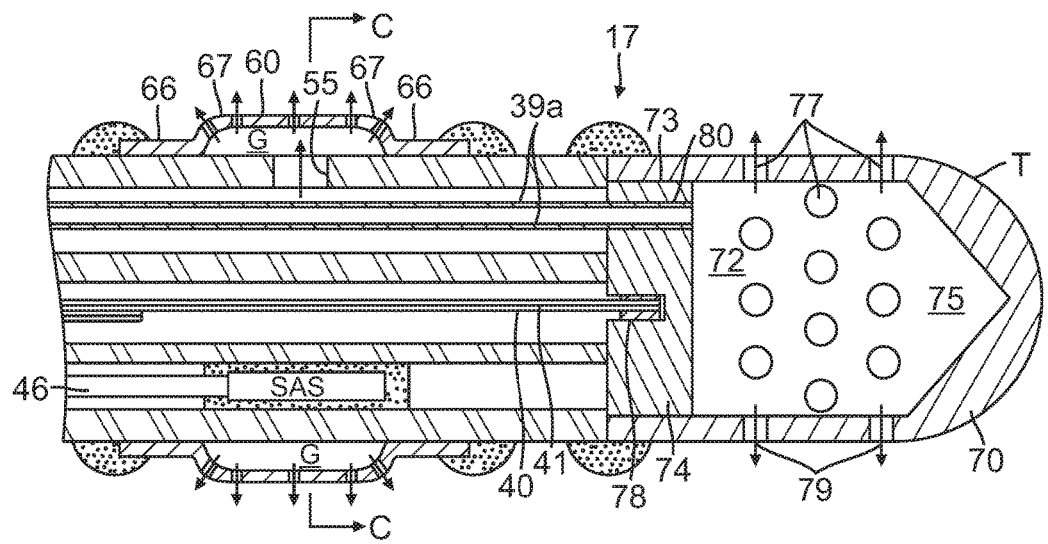
FIG. 6A is a partial side cross-sectional view of the distal section of FIG. 5 taken along a diameter.
Figure 6B:
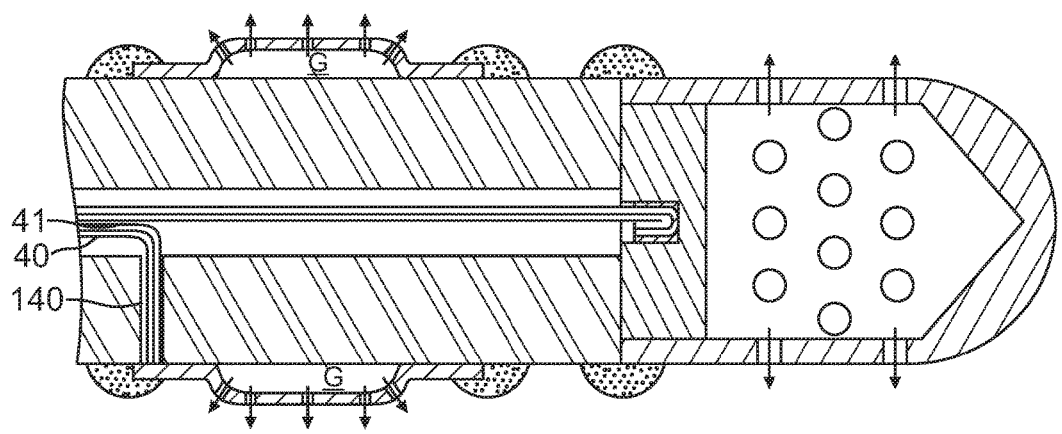
FIG. 6B is a partial side cross-sectional view of the distal section of FIG. 5, taken along another diameter.
Figure 6C:
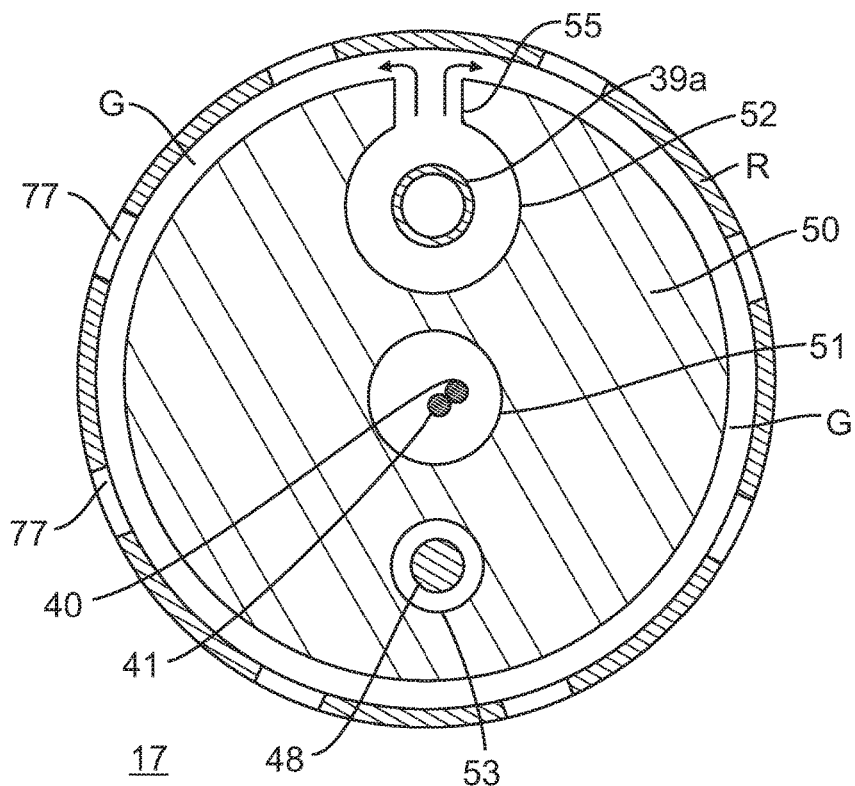
FIG. 6C is an end cross-sectional view of the distal section of FIG. 5, taken along line C-C.
Figure 7:
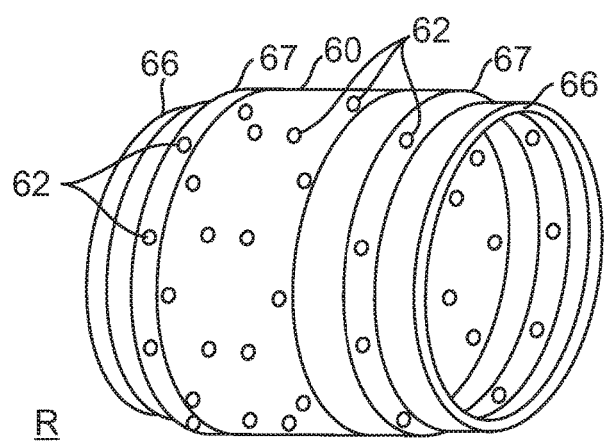
FIG. 7 is an embodiment of an irrigated ring electrode.

With reference to FIGS. 6A, 6B, the ring electrode R is adapted for ablation and irrigation. The ring electrode is generally cylindrical with a length greater than its diameter. The ring electrode has a side cross-section that can resemble a barrel with a side wall 60 that bulges radially between opposing end portions 66. Curved transitional regions 67 are provided between the side wall 60 and the end portions 66 to provide an atraumatic profile without corners or sharp edges.

With reference to FIG. 6C, a reservoir or annular gap G exists around the exterior of the tubing 50 of the distal section 17. The gap G provides improved fluid distribution from the second lumen 52 to the exterior of the ring electrode via apertures 62. The size of the opening 55 in the tubing 50 varies with the position along the length of the distal section 17. For optimum flow, the more distal an opening 55 is along the distal section 17, the greater the size or cross-section of the opening and/or the plurality of openings 55 under each ring electrode.

The apertures 62 are arranged the side wall 60 in a predetermined pattern including axially offset rows. These apertures face outwardly promoting flow in a radial direction (see arrows 63). Apertures are also provided in or near the curved transitional regions 67 to promote flow more in an axial direction (see arrows 64). Moreover, these apertures are particularly effective in minimizing charring and coagulation at or near the curved transitional regions 67 which are likely to be "hot spots" resulting from higher current densities due to transitions in the electrode profile. In that regard, the plurality and/or cross-section of the apertures 62 is greater at or near the curved transitional regions 67 than in the side wall 60 of the electrode so as to provide more cooling in the curved transitional regions. Other suitable ring electrodes are described in US Patent Application Publication No. US2010/0168548 A1, and US patent application Ser. No. 13/174,742, filed Jun. 30, 2011, the entire content of both of which are hereby incorporated by reference.

The tip electrode T on a distal end of the tubing 50 of the distal section 17 has a shell 70 having a U-shaped cross section defining an interior cavity 72 with an open proximal end 73 that is sealed by a plug 74 to form a plenum chamber 75 in the tip electrode. A plurality of irrigation apertures 77 are formed in radial wall of the shell to allow fluid which collects in the plenum chamber to exit to outside of the tip electrode (see arrows 79).

Figure 8:
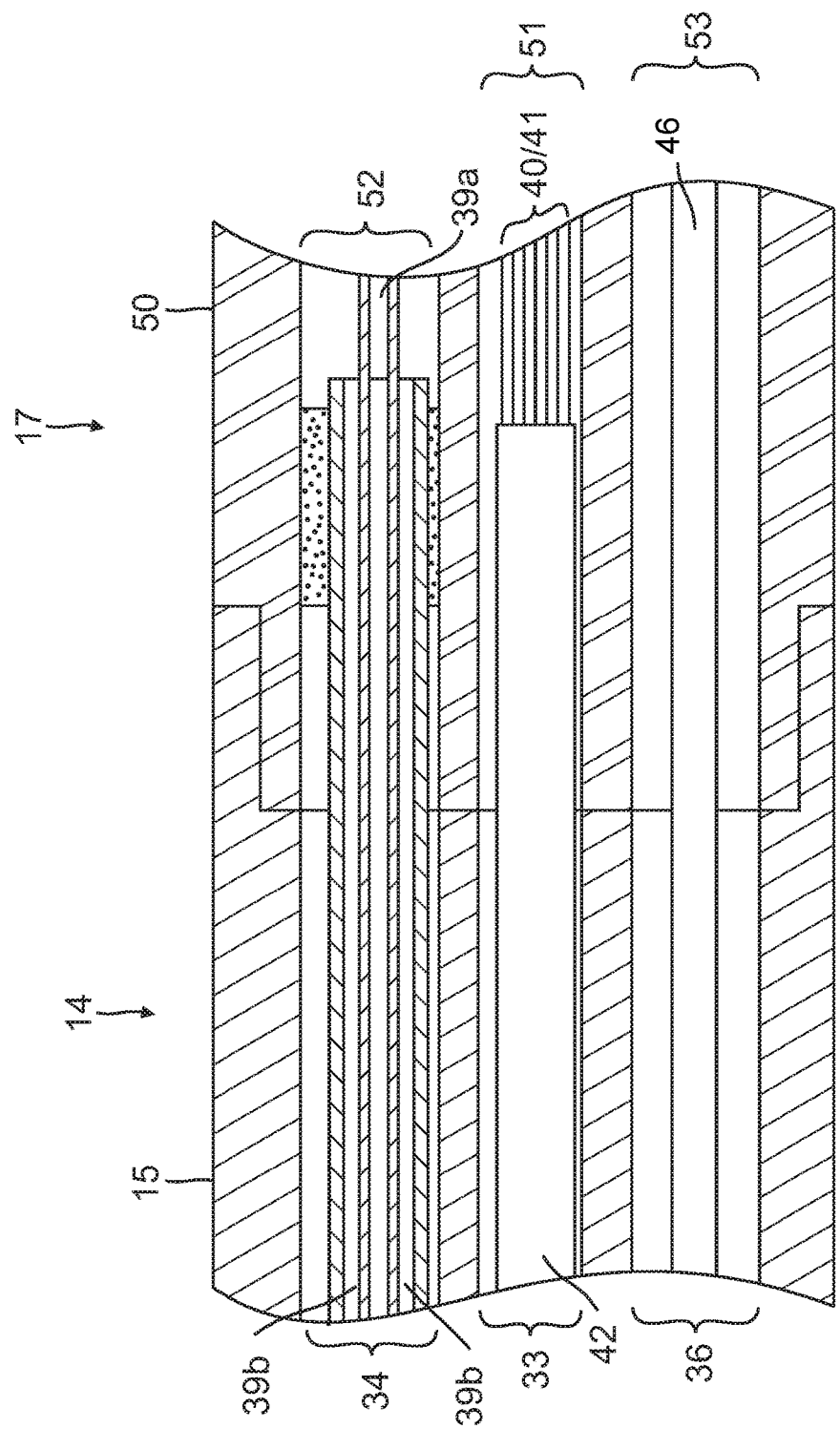
FIG. 8 is a side cross-sectional view of an embodiment of a junction between the intermediate section and the distal section of a catheter in accordance with the present invention.

An axial passage 80 formed in the plug 73 receives the inner lumen 39a of the coaxial irrigation tubing 43. As depicted in FIG. 8, a distal end of the outer lumen 39b terminates a short distance distal of the junction of the tubing 15 of the intermediate section 14 and the tubing 50 of the distal section 17 so that fluid delivered in the outer lumen 39b flows directly into the second lumen 52 of the tubing 50. A sealant can be used to form a fluid-tight seal around the distal end of the outer lumen 39b.

In the illustrated embodiment, the inner lumen 39a extends through the passage 80 and terminates at or near a distal face of the plug 74 so that fluid passing through the inner lumen 39a feeds into the plenum chamber 75. A sealant can be used to around the distal end of the inner lumen 39a in the passage 80. The plug 74 is sized to form a fluid tight seal at the open end 73. The plug 74 also has a blind hole 78 formed on the proximal face to receive a lead wire/thermocouple pair 40, 41 for electrical communication with the tip electrode. To that end, both the plug 74 and shell 70 are made of electrically-conductive material so that electrical energy can pass between the lead wires and the shell. Like the ring electrodes, the tip electrode can be made of any suitable noble metal, such as platinum or gold, preferably a combination of platinum and iridium or gold and platinum.

In accordance with a feature of the present invention, the catheter 10 is adapted to provide separate and dedicated irrigation flow pathways to different electrodes or different sets of electrodes. The selection and division among electrodes can be made on the bases of position of an electrode (e.g., distal or proximal) and/or its type or function (e.g., tip/ring, uni-polar/bi-polar, or focal/connecting). In the disclosed embodiment, the division among electrodes is made between the distal tip electrode and all proximal ring electrodes, such that a first flow pathway is dedicated to supplying the tip electrode to the exclusion of the ring electrodes, and a second flow pathway is dedicated to supplying all the ring electrodes to the exclusion of the tip electrode. It is understood by one of ordinary skill in the art that the division may also be made based solely on position among a distal section of a catheter that carries a plurality of electrodes of an identical type or function. For example, on a distal section with ring electrodes only, a first flow pathway can be dedicated to supplying a proximal portion of the ring electrodes, and a second flow pathway can be dedicated to supplying a distal portion of the ring electrodes.

With reference to FIGS. 2, 4A and 4B, in the disclosed embodiment, the coaxial irrigation tubing 38 extends from the second lumen 52 of the tubing 50 of the distal section 17, the second lumen 34 of the tubing 15 of the intermediate section 14, the central lumen 18 of the catheter body 12, and the control handle 16. In accordance with a feature of the present invention, the proximal end of the coaxial irrigation tubing 38 extends proximally past the control handle 16 and terminates in a flow-balancing valve 90 which controls the flow of fluid into the catheter.

An embodiment of the flow-balancing valve 90 is shown in detail in FIGS. 9, 9A-9D and 10. The valve has a two-piece, generally cylindrical body 92 and a plunger assembly 94. The body includes a proximal body portion 92a and a distal body portion 92b. The proximal portion 92a has an open outer circumferential end 93 that receives an open inner circumferential end 95 of the distal portion. When joined, the portions 92a, 92b are configured to define an enlarged interior flow cavity 96 connecting an inlet opening 97 formed in the proximal portion 92a and an outlet opening 92b formed in the distal portion 92b. The inlet and outlet openings are axially aligned along a longitudinal axis 100 of the body 92. Between the inlet opening and the cavity and also between the cavity and the outlet opening are funnel-shaped transitional regions 101, 102 where cross-sections of the flow path therethrough changes rapidly. From the inlet opening to the cavity, the cross-section increases rapidly. From the cavity to the outlet opening, the cross-section decreases rapidly.

The plunger assembly 94 is axially aligned with the longitudinal axis 100. The plunger assembly includes a plunger head 105 situated in the proximal portion 92a and a base 106 fixedly mounted in the distal portion 92b. Extending between the plunger head and the base is an elastic or spring member 107 (e.g., a coil spring) with a predetermined rate or spring constant. Opposing ends of the spring member are anchored around axially-aligned stem projections 108 formed on the distal face of the plunger head 105 and the proximal face of the base 106. Aligned with the axis 100 are axial through-holes 104 and 109 formed in the plunger head and base, respectively, to receive the inner lumen 39a which extends through the spring member 107 connecting the plunger head and the base.

Figure 9:
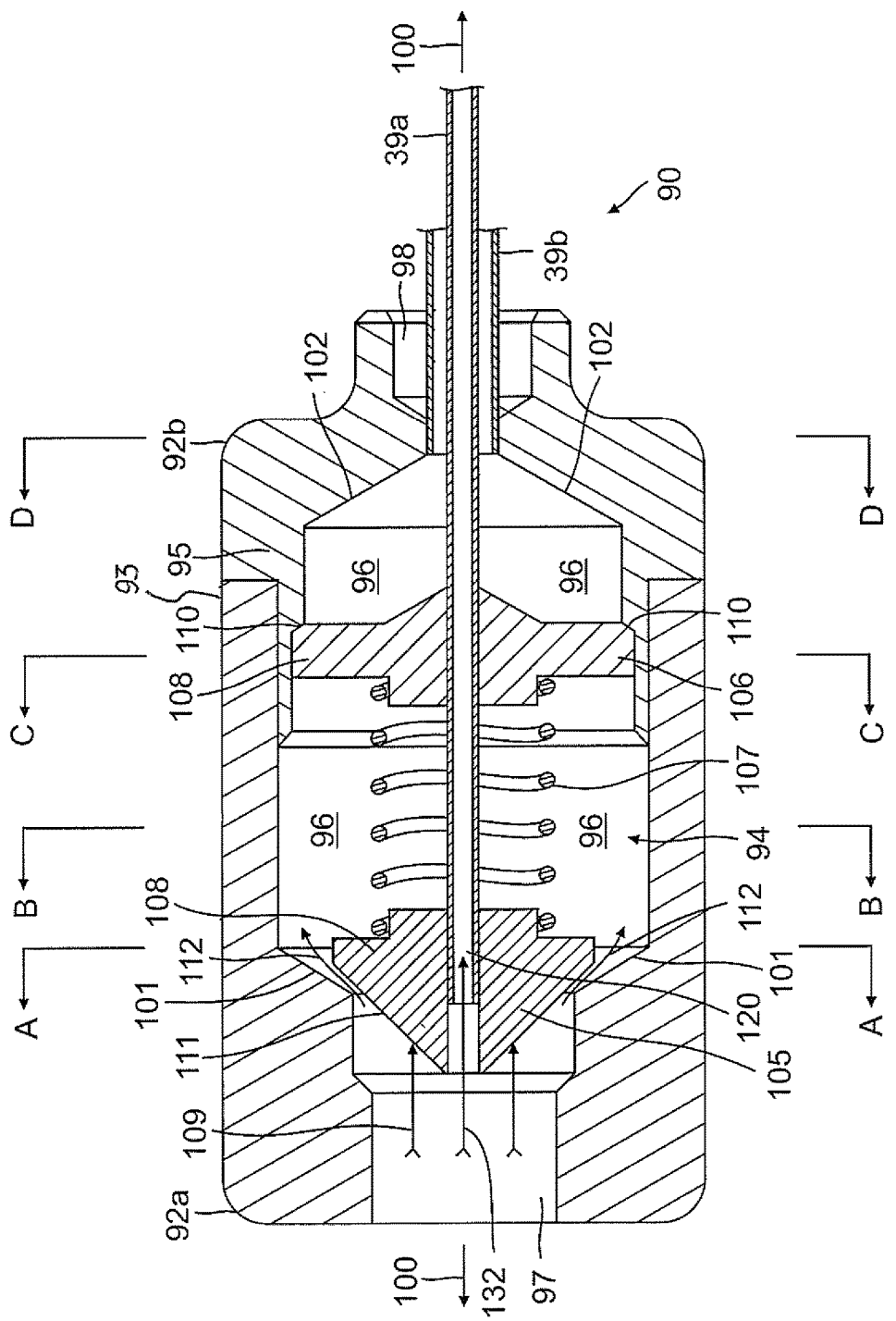
FIG. 9 is a side cross-sectional view of an embodiment of a valve in accordance with the present invention, showing a plunger assembly in one configuration.
Figure 9A:
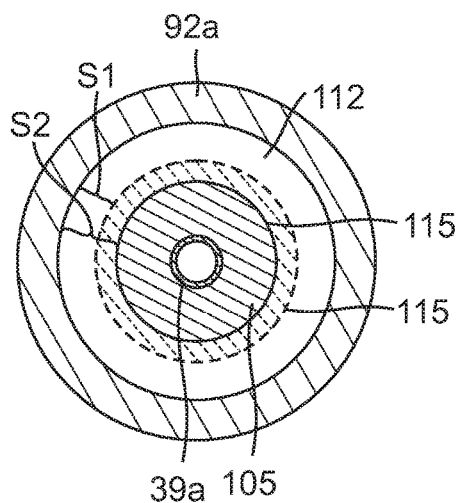
FIGS. 9A-9D are end cross-sectional views of the valve of FIG. 9, taken along lines A-A, B-B, C-C, and D-D, respectively.
Figure 9B:
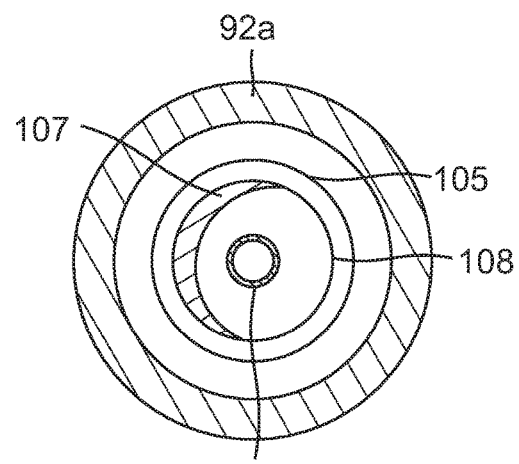

The inlet opening and the outlet opening define a flow direction through the valve (for example, from left to right as shown in FIG. 9). Thus, the outlet opening is downstream of the inlet opening and the inlet opening is upstream of the outlet opening. It is understood that other components of the valve can be similarly described in terms of this flow direction.

Figure 10:
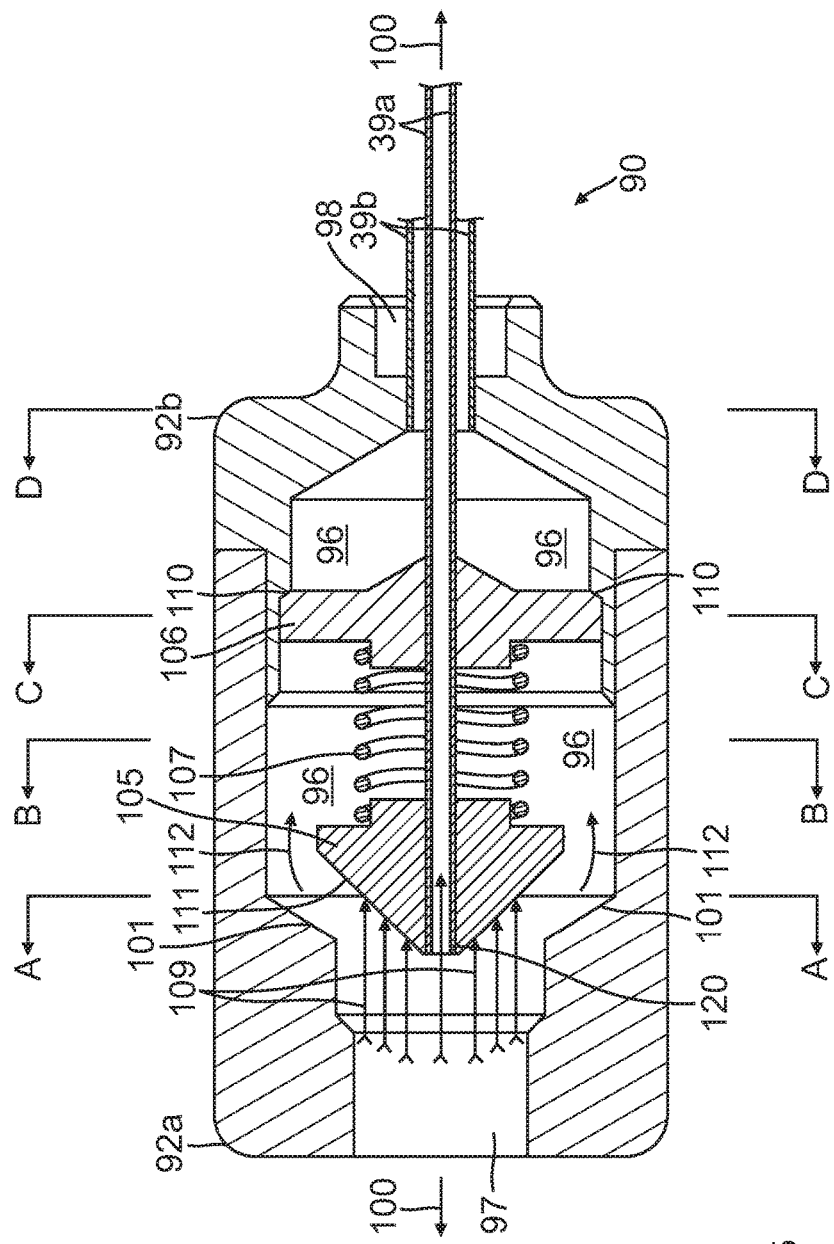
FIG. 10 is a side cross-sectional view of the valve of FIG. 9, showing the plunger assembly in another configuration.

The plunger assembly 94 is configured to receive a generally axial force (arrows 109) onto the plunger head (FIG. 9) which compresses the spring member 107 and displaces the plunger head 105 toward the base 106 and away from inlet transitional region 101 (FIG. 10). The base 106 is fixedly positioned in the distal portion 92b and is wedged against a flange 110 to prevent distal displacement relative to the body. The plunger head has a generally convex profile for dispersing fluid radially and axially over its proximal surface into the cavity 96 to define a fluid region 112 that is generally annular around a periphery 115 of the plunger head 105. In the disclosed embodiment, the plunger head is conical although it could be a variety of shapes, including spherical or even planar.

Figure 11:
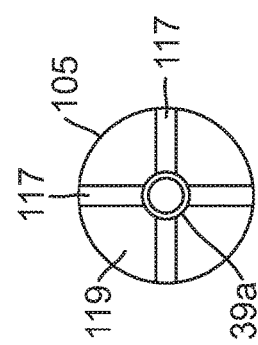
FIG. 11 is an end view of an embodiment of a proximal face of a plunger head.

The size and shape of the inlet transitional region 101 generally correspond with the shape and size of the plunger head 105 to promote flow and minimize turbulence in the flow region 112. Thus, the inlet transitional region has a generally concave profile. However, it is preferable that the size and shape do not correspond exactly so that the flow region 112 through the inlet transitional region is never entirely occluded by the plunger head 105 against the region 101. That is, even if all electrodes are inactive, it is usually desirable that at least a minimum flow be maintained through the electrodes during an ablation procedure to flush the electrodes and keep them free from debris. To that end, channels or grooves 117 can be formed on proximal surface 119 of the plunger head 105 (FIG. 11) to vary or increase the flow distribution from the inlet opening 97 to the cavity 96.

Figure 9C:
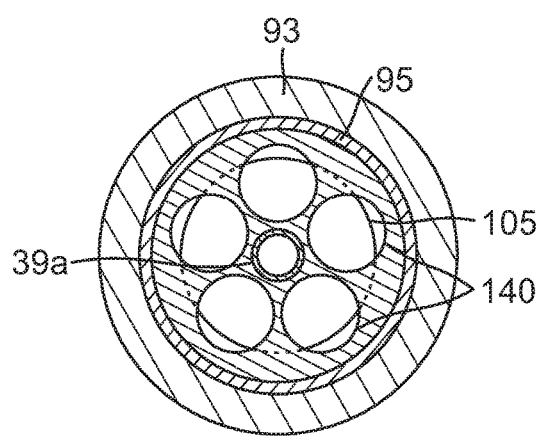
Figure 9D:
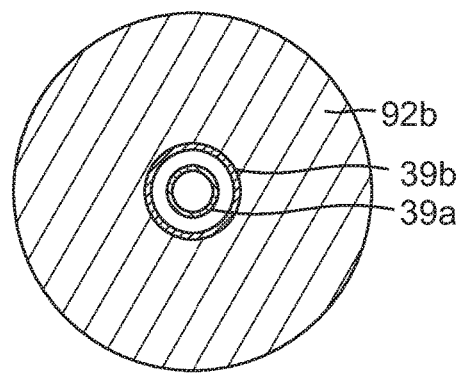

The inlet opening 96 is configured to receive a luer hub 128 connected to fluid tubing 130 extending from fluid source FS as shown in FIG. 2. Thus, fluid is pumped by irrigation pump 27 from fluid source FS to pass into the fluid tubing 130, the luer hub 128, and the inlet opening 97 where it flows onto the plunger head 105. Advantageously, a portion of the fluid entering the valve 90 enters the inner lumen 39a (arrow 132) and a portion is diverted by the plunger head 105 into the cavity 96 (arrow 112). As shown in FIG. 9C, the base is formed with one or more through-holes 140 so that the dispersed fluid can pass through the base 106 and exit the cavity 96 via the outlet opening 98.

Where the flow rate generated by the pump 27 that enters the valve 90 is at or less than a predetermined rate, the fluid merely enters the inner lumen 39a or passes around the plunger head 105 without displacing it. However, where the flow rate is greater the predetermined rate, not only does the flow rate into the inner lumen 39a increases but the fluid exerts a force sufficient to overcome the spring member 107 and depress the plunger head 105 toward the base 106 thus increasing a space separation between the plunger head and the inlet transitional region from S1 to S2 (as better shown in FIG. 9A). With a larger annular flow region 112 around the plunger head 105, there is a greater flow rate through the cavity 96 and hence through the outlet opening 98 into the outer lumen 39b. In that regard, the plunger head can freely slide on the outer surface of the inner lumen 39a without interfering with the compression of the plunger head toward the base. As such, it is also understood that the inner lumen 39a may require a structure with a certain amount of rigidity to maintain axial alignment between the plunger head and the base. For example, the portion of the inner lumen 39a that extends through the valve may be made of a stiffer material than the portion of the inner lumen 39a that extends through the control handle or any other part of the catheter, including the catheter body 12, intermediate section 14 and distal section 17.

The valve 90 thus provides two separate fluid paths between the inlet opening 101 and the outlet opening 102. An unimpeded portion enters the lumen 39a defining a first fluid path. The remaining portion is diverted by the plunger head 105 toward the fluid region 112 and enters the interior cavity where it passes through the base 106 via the through-holes 140 toward the outlet opening. Where the plunger head is displaced under greater pressure from fluid impacting its proximal surface, the flow amount/flow rate of the second flow path changes accordingly as the fluid region 112 expands and more fluid enters into the cavity.

In the disclosed embodiment, irrigation fluid is delivered to the tip electrode by the inner lumen 39a which extends into the tip electrode, and irrigation fluid is delivered to the ring electrodes by the outer lumen 39b which terminates in the second lumen 52 of the tubing 50 of the distal section. The coaxial irrigation tubing 38 having at least the lumens 39a and 39b extends through the second lumen 32 of the tubing 15 of the intermediate section, the central lumen 18 of the catheter body 12, and through the control handle 16.

The proximal end of each electrode lead wire is electrically connected to a suitable connector at the distal end of the control handle 16 for connection to the RF generator 11. A pair of wires 40, 41 is provided for each electrode. In the disclosed embodiment, wire 40 of the wire pair is a copper wire, e.g. a number "40" copper wire and the wire 41 is a constantan wire. The wires of each pair are electrically isolated from each other except at their distal ends where they are twisted together. Attachment to the respective ring electrode R is accomplished by feeding the wire pair through a hole 140 formed in the side wall into the first lumen 51 of the tubing 50 of the distal section 17, and soldering to the respective ring electrode (see FIG. 6B). The wire pairs for each electrode (ring and tip) extend distally from the control handle 16, through the central lumen 18 of the catheter body 12, the first lumen 33 of the intermediate section 14, and the first lumen 51 of the distal section 17. RF energy, is delivered to the electrodes via the wire 40 of the wire pairs. However, as understood by one of ordinary skill in the art, the wire pairs inclusive of their respective constantan wire can also function as temperature sensors or thermocouples sensing temperature of each electrode.

All of the wire pairs pass through a common nonconductive protective sheath 42 (FIG. 4C), which can be made of any suitable material, e.g., polyimide, in surrounding relationship therewith. The sheath 42 extends from the control handle 16, the catheter body 12, the intermediate section 14, and terminates just distal of the proximal end of the distal section 17. The distal end is anchored in the first lumen 51 by glue, for example, polyurethane glue or the like.

The pair of deflection puller wire 44a, 44b are provided for deflection of the intermediate shaft 14. The puller wires 44a, 44b extend through the central lumen 18 of the catheter body 12 and each through a respective one of the third and sixth lumens 35 and 38 of the intermediate section 14. They are anchored at their proximal ends in the control handle 16, and at their distal end to a location at or near the distal end of the intermediate section 14 by means of T-bars 142 (FIG. 4C) that are affixed to the sidewall of the tubing 15 by suitable material 103, e.g., polyurethane, as generally described in U.S. Pat. No. 6,371,955, the entire disclosure of which is incorporated herein by reference. The puller wires are made of any suitable metal, such as stainless steel or Nitinol, and is preferably coated with Teflon® or the like. The coating imparts lubricity to the puller wire. For example, each puller wire has a diameter ranging from about 0.006 to about 0.010 inch.

As seen in FIGS. 4A and 4B, each puller wire has a respective compression coil 144 in surrounding relation thereto. Each compression coil 144 extends from the proximal end of the catheter body 12 to at or near the proximal end of the intermediate section 14 to enable deflection. The compression coils are made of any suitable metal, preferably stainless steel, and are each tightly wound on itself to provide flexibility, i.e., bending, but to resist compression. The inner diameter of the compression coils is preferably slightly larger than the diameter of a puller wire. The Teflon® coating on the puller wire allows it to slide freely within the compression coil. Within the catheter body 12, the outer surface of the compression coil is covered by a flexible, non-conductive sheath 152, e.g., made of polyimide tubing. The compression coils are anchored at their proximal ends to the outer wall 30 of the catheter body 12 by proximal glue joints and to the intermediate section 14 by distal glue joints.

Within the third and fifth lumens 35, 37 of the intermediate section 14, the puller wires 44a, 44b extend through a plastic, preferably Teflon®, puller wire sheath 146 (FIG. 4B), which prevents the puller wires from cutting into the wall of the tubing 15 of the intermediate section 14 when the intermediate section 14 is deflected.

Longitudinal movement of the puller wires 44a, 44b relative to the catheter body 12 for bi-directional deflection is accomplished by appropriate manipulation of the control handle 16. A deflection knob 150 (FIG. 1) is provided on the handle which can be pivoted in a clockwise or counterclockwise direction for deflection in the same direction. Suitable control handles for manipulating more than one wire are described, for example, in U.S. Pat. Nos. 6,468,260, 6,500,167, and 6,522,933 and U.S. application Ser. No. 12/960,286, filed Dec. 3, 2010, the entire disclosures of which are incorporated herein by reference.

In one embodiment, the position sensor 48 includes a plurality of single axis sensors ("SAS") carried on the cable 46 that extends through the third lumen 46 of the distal section 17 (FIG. 4C), where each SAS occupies a known or predetermined position along the length of the distal section. The cable 46 extends proximally from the distal section 17 through the fourth lumen 36 of the intermediate section 14 (FIG. 6), the central lumen 18 of the catheter body 12, and into the control handle 16. Each SAS can be positioned with a known and equal spacing separating adjacent SASs. In the disclosed embodiment, the cable carries three SASs that are positioned under the distal-most ring electrode (FIG. 6A), the proximal-most ring electrode, and a mid ring electrode, for sensing location and/or position of the distal section. The SASs enable the distal section to be viewed under mapping systems manufactured and sold by Biosense Webster, Inc., including the CARTO, CARTO XP and NOGA mapping systems. Suitable SASs are described in U.S. application Ser. No. 12/982,765, filed Dec. 30, 2010, the entire disclosure of which is incorporated herein by reference.

Figure 12:
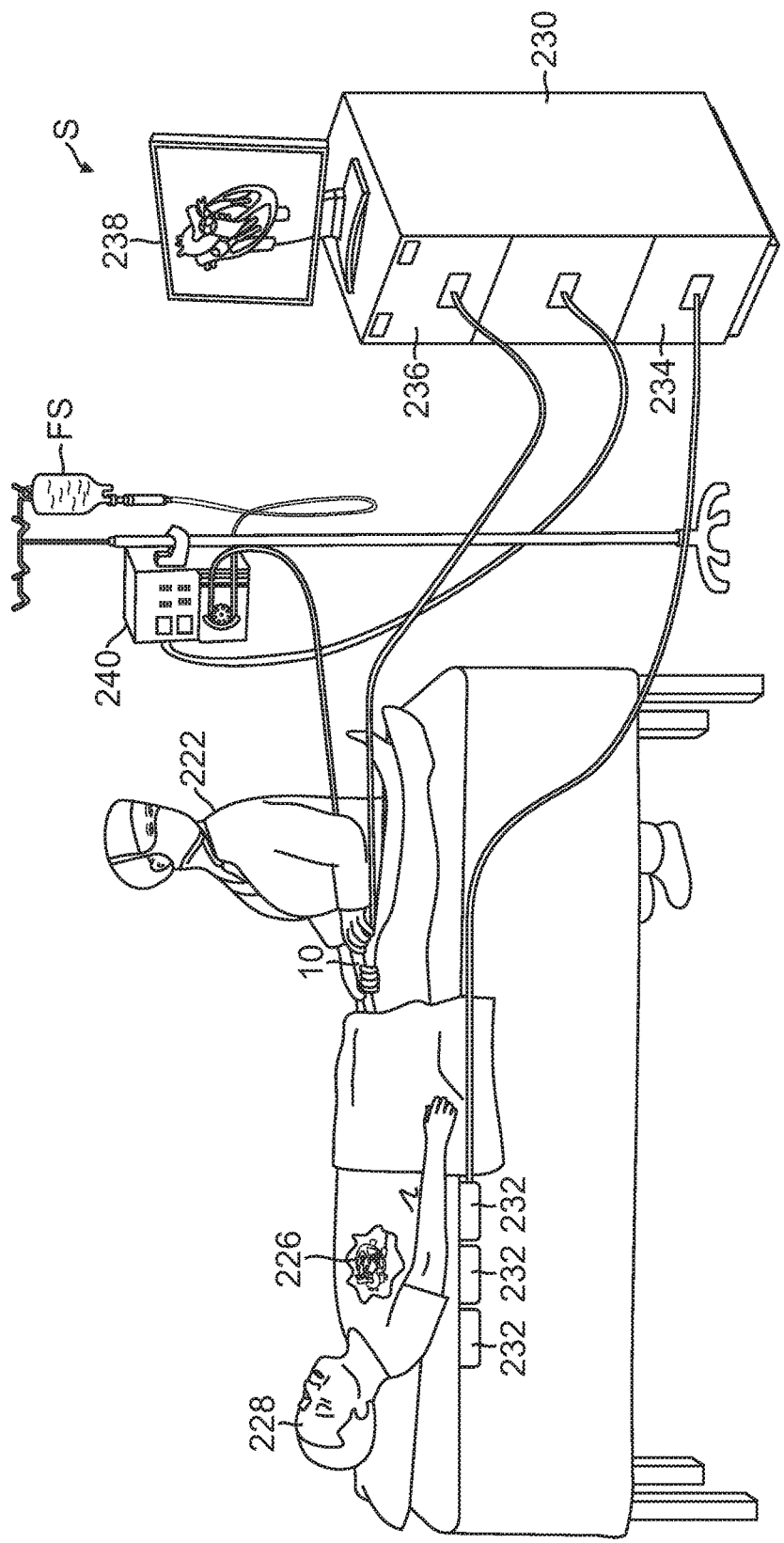
FIG. 12 is a schematic pictorial illustration of a system for ablation of tissue in the heart, in accordance with an embodiment of the present invention.

FIG. 12 is a schematic pictorial illustration of a system S for ablation of tissue in a heart 226 of a patient 228, in accordance with an embodiment of the present invention. An operator 222, such as a cardiologist, inserts a catheter 10 through the vascular system of the patient so that the distal end of the catheter enters a chamber of the patient's heart. Operator advances the catheter so that the distal section 17 of the catheter engages endocardial tissue at a desired location or locations, as shown in FIG. 5. Catheter 10 is connected by a suitable connector at its proximal end to a console 230. The console comprises an RF generator 236 for applying RF energy through tip and ring electrodes on the distal section of the catheter in order to ablate the tissue contacted by the distal section.

Responsive to signals from the RF generator 236 representing the energization states of each electrode on the catheter, an irrigation pump 240 with a pump head is adapted to provide irrigation fluid to the catheter at different flow rates to provide suitable irrigation fluid to the electrodes. Because the coaxial irrigation tubing 38 defines at least two separate fluid flow pathways with the valve 90 actively balancing the two flows, selected electrode(s) or sets of electrodes are supplied fluid at different rates, and preferably in accordance with the energization states of the electrodes.

FIG. 12 is a table of sample flow rates for different operating conditions for one embodiment of the system S, explained as follows:

Condition 1: During maintenance flow, the irrigation pump is set to flow rate of 8 mL/min. As the fluid flow enters the valve, it is directed into the inner lumen 39a which supplies the tip electrode and ring electrodes.

Condition 2: During focal ablations, the irrigation pump is set to a flow rate of 21 mL/min. The pressure difference across the plunger head is not sufficient to displace the plunger head. The majority of flow is directed to inner lumen 39a supplying the tip electrode allowing for a flow rate of approximately 15 mL/min while the ring electrodes are supplied with a maintenance flow.

Condition 3: During linear ablations, the irrigation pump is set to a flow rate of 33 mL/min. The pressure difference across the plunger head is sufficiently high to displace the plunger head allowing for increased flow to the ring electrodes.

In the pictured embodiment, system S uses magnetic positioning sensing to determine position coordinates of the distal assembly of the catheter inside heart. To determine the position coordinates, a driver circuit 234 in console 230 drives field generators 232 to generate magnetic fields within the body of patient. Typically, field generators comprise coils, which are placed below the patient's torso at known positions external to the body. These coils generate magnetic fields in a predetermined working volume that contains heart. One or more magnetic field sensors, such as the SASs, within the distal section of the catheter generate electrical signals in response to these magnetic fields. The console 230 processes these signals in order to determine the position (location and/or orientation) coordinates of the distal section 17 of the catheter. Console may use the coordinates in driving a display 238 to show the location and status of the catheter. This method of position sensing and processing is described in detail, for example, in PCT International Publication WO 96/05768, whose entire disclosure is incorporated herein by reference, and is implemented in the CARTO system produced by Biosense Webster Inc. (Diamond Bar, California).

The operator may first pass a sheath percutaneously through the vascular system and into the heart through the ascending vena cava. The catheter is then inserted through the sheath until the distal section 17 of the catheter extends past the distal end of the sheath and is exposed for contact with the target tissue in the heart. The operator may rotate the control handle and/or use the deflection knob 150 of the control handle 16 to maneuver catheter in directing the distal section 17 toward the target tissue. The operator may carry out this alignment using the position sensing methods described above, along with a pre-acquired map or image of heart as displayed on the display 238. Alternatively or additionally, the alignment may be performed under fluoroscopic or other means of visualization.

With reference to FIG. 5, the catheter 10 is well adapted to form linear or continuous lesions, such as a "roof line" in the left atrium. For example, when the tip electrode T and ring electrodes R1-RN of the distal section 17 are positioned in contact with the target tissue, the tip electrode T and ring electrodes R are energized (with the latter energized as uni-polar electrodes) to ablate and form a plurality of focal lesions 110 (solid lines). Being in communication with and responsive to the RF generator, the irrigation pump activates the motor control of the pump head to supply the tip and ring electrodes with fluid arriving at the valve 90 at a selected flow rate which the valve effectively splits into at least two separate flow paths with different flow rates exiting the valve. For example, where only the tip electrode is energized (such as for focal unipolar ablation) and the ring electrodes are inactive, the RF generator 236 signals the pump 240 pump fluid to the valve 90 at an appropriate selected flow rate that would avoid displacement of the plunger head so that a minimum flow passes around the plunger head toward the outer lumen 39b to merely flush the ring electrodes, while a greater flow enters the inner lumen 39a to cool the tip electrode. The minimum flow advantageously minimizes fluid load on the patient.

In contrast, where the tip electrode and the ring electrode are energized (such as for linear ablation by means of uni-polar and bi-polar ablation), the RF generator signals the pump to pump fluid to the valve at a greater selected flow rate that would distally displace the plunger head 105 so that a greater flow passes around the plunger head toward the outer lumen 39b to provide more fluid for cooling the ring electrodes. A greater flow may pass into the inner lumen 39a to provide fluid for cooling the tip electrode. The valve therefore acts on the fluid entering with a predetermined flow rate to split and balance the fluid so that it exits in two different separate and independent paths with two different flow rates.

Advantageously, the catheter 10 remains in the same position and need not be dragged or repositioned as a continuous lesion is formed by focal lesions 110 (solid lines) by the electrode energized as uni-polar electrodes and then by connecting lesions 112 (broken lines) by the electrode energized as bi-polar electrodes. Because the catheter need not be repositioned, ablation procedure time is reduced and clinical efficacy is improved.

If touch up of broken or incomplete lesion lines is desired, the catheter can be repositioned such that the tip electrode T forms additional focal lesions to complete the linear or continuous lesion. With only the tip electrode energized, the irrigation pump signals the motor control of the pump head to reduce the flow rate so that the plunger head is not depressed and the ring electrodes receive only a minimal flow via the outer lumen 39b for flushing purposes while the tip electrode receives sufficient flow for cooling via the inner lumen 39a.

Although FIG. 12 shows a particular system configuration, other system configurations may be used in alternative embodiments of the present invention. For example, the methods described hereinbelow may be applied using position transducers of other types, such as impedance-based or ultrasonic position sensors. The term "position transducer" as used herein refers to an element mounted on or in catheter that causes console to receive signals indicative of the coordinates of the element. The position transducer may thus comprise a received in the catheter, which generates a position signal to the control unit based on energy received by the transducer; or it may comprise a transmitter, emitting energy that is sensed by a receiver external to the probe. Furthermore, the methods described hereinbelow may similarly be applied in mapping and measurement applications using not only catheters, but also probes of other types, both in the heart and in other body organs and regions.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Any feature or structure disclosed in one embodiment may be incorporated in lieu of or in addition to other features of any other embodiments, as needed or appropriate. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising:
   an elongated body;
   a distal section having at least a first electrode and a second electrode, each electrode adapted for irrigation;
   a control handle proximal the elongated body;
   a coaxial irrigation tubing having at least an inner lumen and an outer lumen, the inner lumen dedicated to transporting fluid to the first electrode, and the outer lumen dedicated to transporting fluid to the second electrode; and a common valve comprising a moveable member, an inlet opening and an outlet opening, the outlet opening being fluidly connected to both the inner lumen and the outer lumen of the coaxial irrigation tubing, the common valve having first and second separate fluid flow pathways between the inlet opening and the outlet opening, the second fluid flow pathway extending around an exterior surface of the moveable member and into the outer lumen, the first fluid pathway extending through the moveable member and in the inner lumen, and the moveable member being configured to automatically move in response to a threshold fluid force to thereby enlarge or expand the second fluid flow pathway.

2. A catheter of claim 1, wherein the first electrode is a tip electrode and the second electrode is a ring electrode.

3. A catheter of claim 2, wherein the second electrode comprises at least two ring electrodes and the outer lumen of the coaxial irrigation tubing is configured to transport fluid to the at least two ring electrodes.

4. A catheter of claim 1, wherein the first and second separate fluid flow pathways are isolated from each other within the catheter.

* * * * *